(12) United States Patent
Hrabie et al.

(10) Patent No.: US 7,968,664 B2
(45) Date of Patent: Jun. 28, 2011

(54) NITRIC OXIDE-RELEASING DIAZENIUMDIOLATED ACRYLONITRILE-BASED POLYMERS, AND COMPOSITIONS, MEDICAL DEVICES, AND USES THEREOF

(75) Inventors: Joseph A. Hrabie, Frederick, MD (US); Michael L. Citro, Harpers Ferry, WV (US); Frank DeRosa, Nanuet, NY (US); Larry K. Keefer, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1078 days.

(21) Appl. No.: 11/576,012

(22) PCT Filed: Sep. 27, 2005

(86) PCT No.: PCT/US2005/035065
§ 371 (c)(1),
(2), (4) Date: May 15, 2007

(87) PCT Pub. No.: WO2006/037105
PCT Pub. Date: Apr. 6, 2006

(65) Prior Publication Data
US 2007/0292471 A1    Dec. 20, 2007

Related U.S. Application Data

(60) Provisional application No. 60/613,257, filed on Sep. 27, 2004.

(51) Int. Cl.
*A61F 2/02* (2006.01)
*A61K 31/785* (2006.01)
*A61P 9/00* (2006.01)
*A61P 9/10* (2006.01)
*A61P 9/12* (2006.01)
*C07D 211/72* (2006.01)
*C07D 471/04* (2006.01)
*C07D 471/14* (2006.01)
*C07F 7/02* (2006.01)
*C08F 222/30* (2006.01)

(52) U.S. Cl. ............ 526/341; 424/426; 424/78.35; 424/423; 564/512; 546/122; 546/14; 546/297; 546/307; 546/82

(58) Field of Classification Search ............ 526/341, 526/346, 335, 317.1, 319, 332, 297, 310, 526/242, 280; 424/423, 426, 78.35; 546/122, 546/14, 297, 307, 82; 564/512
See application file for complete search history.

(56) References Cited

U.S. PATENT DOCUMENTS
5,272,231 A * 12/1993 Campbell et al. ............ 526/236
(Continued)

FOREIGN PATENT DOCUMENTS
EP       1 300 424 A1    4/2003
(Continued)

OTHER PUBLICATIONS
Arnold et al., *Tetrahedron Letters*, 41, 8421-8424 (2000).
(Continued)

*Primary Examiner* — William K Cheung
(74) *Attorney, Agent, or Firm* — Leydig, Voit & Mayer, Ltd.

(57) ABSTRACT

The invention described herein provides for novel nitric oxide-releasing polymers that comprise at least two adjacent units derived from acrylonitrile monomer units and containing at least one carbon-bound diazeniumdiolate. The diazeniumdiolated acrylonitrile-derived polymers can be used in medical devices therapeutically. Accordingly, the invention also provides a method of treating a biological disorder and a method of promoting angiogenesis that includes administering a medical device comprising a nitric oxide-releasing polymer comprising at least two adjacent units of acrylonitrile before exposure to nitric oxide and at least one nitric oxide releasing $N_2O_2$— group, wherein the $N_2O_2$— group is attached directly to the polyacrylonitrile backbone, to a specific location on or within the mammal in an amount effective to treat the biological disorder or promote angiogenesis.

16 Claims, 8 Drawing Sheets

U.S. PATENT DOCUMENTS

| | | | |
|---|---|---|---|
| 5,405,919 | A | 4/1995 | Keefer et al. |
| 5,525,357 | A | 6/1996 | Keefer et al. |
| 5,632,981 | A | 5/1997 | Saavedra et al. |
| 5,650,447 | A | 7/1997 | Keefer et al. |
| 5,674,894 | A | 10/1997 | Currie et al. |
| 5,676,963 | A | 10/1997 | Keefer et al. |
| 5,691,423 | A | 11/1997 | Smith et al. |
| 5,718,892 | A | 2/1998 | Keefer et al. |
| 5,721,365 | A | 2/1998 | Keefer et al. |
| 6,110,453 | A | 8/2000 | Keefer et al. |
| 6,200,558 | B1 | 3/2001 | Saavedra et al. |
| 6,232,336 | B1 | 5/2001 | Hrabie et al. |
| 6,270,779 | B1 | 8/2001 | Fitzhugh et al. |
| 6,511,991 | B2 | 1/2003 | Hrabie et al. |
| 6,673,338 | B1 | 1/2004 | Arnold et al. |
| 6,703,046 | B2 | 3/2004 | Fitzhugh et al. |
| 6,750,254 | B2 | 6/2004 | Hrabie et al. |
| 6,949,530 | B2 | 9/2005 | Hrabie et al. |
| 7,803,395 | B2 * | 9/2010 | Datta et al. ............... 424/426 |
| 2004/0014720 | A1 | 1/2004 | Hrabie et al. |

FOREIGN PATENT DOCUMENTS

| | | |
|---|---|---|
| EP | 1 308 179 A1 | 5/2003 |
| FR | 1 567 710 A | 5/1969 |
| JP | 7 202 4974 B | 4/1970 |
| NL | 7 018 766 A | 6/1971 |
| WO | WO 91/05551 A1 | 5/1991 |
| WO | WO 03/026717 A1 | 4/2003 |
| WO | WO 2004/012874 * | 2/2004 |
| WO | WO 2004/012874 A1 | 2/2004 |

OTHER PUBLICATIONS

Clark, Howard G., *Die Makromolekulare Chemie*, 63, 69-77 (1963).
Mishra, Mahendra Kumar, "Nitric Oxide Initiated Polymerization of Acrylonitrile" *Die Angewandte Makromolekulare Chemie*, 150, 113-122 (1987).
Ozaki et al., *J. Surg. Res.*, 55, 543-547 (1993).
Phaneuf et al., *J. Biomed. Mat. Res.*, 27, 233-237 (1993).
Takata et al., *Chem. of High Polymers*, 16, 693-698 (1959).

* cited by examiner

NITRIC OXIDE-RELEASING DIAZENIUMDIOLATED ACRYLONITRILE-BASED POLYMERS, AND COMPOSITIONS, MEDICAL DEVICES, AND USES THEREOF

This patent application claims the benefit of U.S. Provisional Application No. 60/613,257, filed Sep. 27, 2004.

FIELD OF THE INVENTION

This invention relates to nitric oxide-releasing diazeniumdiolated acrylonitrile-based polymers, to compositions and medical devices comprising such polymers, and to methods of using such compounds, compositions, and medical devices.

BACKGROUND OF THE INVENTION

Many treatments of the vascular system entail the introduction of a device such as a stent, a catheter, a balloon, a wire guide, a cannula, or the like. However, when such a device is introduced into and manipulated through the vascular system, the blood vessel walls can be disturbed or injured. Clot formation or thrombosis often results at the injured site, causing stenosis or occlusion of the blood vessel. Moreover, if the medical device is left within the patient for an extended period of time, thrombus often forms on the device itself, again causing stenosis or occlusion. As a result, the patient is placed at risk of a variety of complications, including heart attack, pulmonary embolism, and stroke. Thus, the use of such a medical device can entail the risk of precisely the problems that its use was intended to ameliorate. Additional complications can arise from these medical procedures. For example, synthetic materials in the blood vessels can also cause platelet aggregation, resulting in some instances in potentially life-threatening thrombus formation.

Nitric oxide has recently been shown to dramatically reduce thrombocyte and fibrin aggregation/adhesion and smooth muscle cell hyperplasia while promoting endothelial cell growth (Cha et al., "Effects of Endothelial Cells and Mononuclear Leukocytes on Platelet Aggregation," *Haematologia* (Budap), 30(2): 97-106 (2000); Lowson et al., "The Effect of Nitric Oxide on Platelets When Delivered to the Cardiopulmonary Bypass Circuit," *Anesth. Analg.*, 89(6): 1360-1365 (1999); Riddel et al., "Nitric Oxide and Platelet Aggregation," *Vitam. Horm.*, 57: 25-48 (1999); Gries et al., "Inhaled Nitric Oxide Inhibits Human Platelet Aggregation, P-selectin expression, and Fibrinogen Binding In Vitro and In Vivo," *Circulation*, 97(15): 1481-1487 (1998); and Lüscher, "Thrombocyte-vascular Wall Interaction and Coronary Heart Disease," *Schweiz Med. Wochenschr.*, 121(51-52): 1913-1922 (1991)).

In addition to its role in promoting angiogenesis and inhibiting thrombosis, NO has been implicated in a variety of bioregulatory processes, including normal physiological control of blood pressure, neurotransmission, cancer, and infectious diseases. See, e.g., Moncada, "Nitric Oxide," *J. Hypertens. Suppl.*, 12(10): S35-39 (1994); Moncada et al., "Nitric Oxide from L-Arginine: A Bioregulatory System," *Excerpta Medica*, International Congress Series 897 (Elsevier Science Publishers B. V.: Amsterdam, 1990); Marletta et al., "Unraveling the Biological Significance of Nitric Oxide," *Biofactors* 2: 219-225 (1990); Ignarro, "Nitric Oxide. A Novel Signal Transduction Mechanism for Transcellular Communication," *Hypertension*, 16: 477-483 (1990); Hariawala et al., "Angiogenesis and the Heart: Therapeutic Implications," *J. R. Soc. Med.*, 90(6): 307-311 (1997); Granger et al., "Molecular and Cellular Basis of Myocardial Angiogenesis," *Cell. Mol. Biol. Res.*, 40(2): 81-85 (1994); Chiueh, "Neuroprotective Properties of Nitric Oxide," *Ann. N.Y. Acad. Sci.*, 890: 301-311 (1999); Wink et al., "The Role of Nitric Oxide Chemistry in Cancer Treatment," *Biochemistry* (Moscow), 63(7): 802-807 (1998); Fang, F. C., "Perspectives Series: Host/Pathogen Interactions. Mechanisms of Nitric Oxide-Antimicrobial Activity," *J. Clin. Invest.*, 99(12): 2818-25 (1997); and Fang, F. C., "Nitric Oxide and Infection," (Kluwer Academic/Plenum Publishers: New York, 1999).

One approach for treating a biological disorder associated with the implantation of a medical device involves prophylactically supplying the injury site with therapeutic levels of NO. This can be accomplished by stimulating the endogenous production of NO or using exogenous NO sources. Methods to regulate endogenous NO release have primarily focused on activation of enzymatic pathways with excess NO metabolic precursors like L-arginine and/or increasing the local expression of nitric oxide synthase (NOS) using gene therapy. U.S. Pat. Nos. 5,945,452, 5,891,459, and 5,428,070 describe the sustained NO elevation using orally administrated L-arginine and/or L-lysine while U.S. Pat. Nos. 5,268,465, 5,468,630, and 5,658,565 describe various gene therapy approaches. Other various gene therapy approaches have been described in the literature. See, e.g., Smith et al., "Gene Therapy for Restenosis," *Curr. Cardiol. Rep.*, 2(1): 13-23 (2000); Alexander et al., "Gene Transfer of Endothelial Nitric Oxide Synthase but not Cu/Zn Superoxide Dismutase restores Nitric Oxide Availability in the SHRSP," *Cardiovasc. Res.*, 47(3): 609-617 (2000); Channon et al., "Nitric Oxide Synthase in Atherosclerosis and Vascular Injury: Insights from Experimental Gene Therapy," *Arterioscler. Thromb. Vasc. Biol.*, 20(8): 1873-1881 (2000); Tanner et al., "Nitric Oxide Modulates Expression of Cell Cycle Regulatory Proteins: A Cytostatic Strategy for Inhibition of Human Vascular Smooth Muscle Cell Proliferation," *Circulation*, 101(16): 1982-1989 (2000); Kibbe et al., "Nitric Oxide Synthase Gene Therapy in Vascular Pathology," *Semin. Perinatol.*, 24(1): 51-54 (2000); Kibbe et al., "Inducible Nitric Oxide Synthase and Vascular Injury," *Cardiovasc. Res.*, 43(3): 650-657 (1999); Kibbe et al., "Nitric Oxide Synthase Gene Transfer to the Vessel Wall," *Curr. Opin. Nephrol. Hypertens.*, 8(1): 75-81 (1999); Vassalli et al., "Gene Therapy for Arterial Thrombosis," *Cardiovasc. Res.*, 35(3): 459-469 (1997); and Yla-Herttuala, "Vascular Gene Transfer," *Curr. Opin. Lipidol.*, 8(2): 72-76 (1997). In the case of preventing restenosis, however, these methods have not proved clinically effective. Similarly, regulating endogenously expressed NO using gene therapy techniques such as NOS vectors remains highly experimental. Also, there remain significant technical hurdles and safety concerns that must be overcome before site-specific NOS gene delivery will become a viable treatment modality.

The exogenous administration of gaseous nitric oxide is not feasible due to the highly toxic, short-lived, and relatively insoluble nature of NO in physiological buffers. As a result, the clinical use of gaseous NO is largely restricted to the treatment of neonates with conditions such as persistent pulmonary hypertension (Weinberger et al., "The Toxicology of Inhaled Nitric Oxide," *Toxicol. Sci.*, 59(1): 5-16 (2001); Kinsella et al., "Inhaled Nitric Oxide: Current and Future Uses in Neonates," *Semin. Perinatol.*, 24(6): 387-395 (2000); and Markewitz et al., "Inhaled Nitric Oxide in Adults with the Acute Respiratory Distress Syndrome," *Respir. Med.*, 94(11): 1023-1028 (2000)). Alternatively, however, the systemic delivery of exogenous NO with such prodrugs as nitroglycerin has long enjoyed widespread use in the medical management of angina pectoris or the "chest pain" associated with atherosclerotically narrowed coronary arteries. There are problems with the use of agents such as nitroglycerin. Because nitroglycerin requires a variety of enzymes and cofactors in order to release NO, repeated use of this agent over short intervals produces a diminishing therapeutic benefit. This phenomenon is called drug tolerance and results from the near or complete depletion of the enzymes/cofactors needed in the blood to efficiently convert nitroglycerin to a NO-releasing species. By contrast, if too much nitroglycerin is initially given to the patient, it can have devastating side effects including severe hypotension and free radical cell damage.

One potential method for overcoming the disadvantages associated with NO prodrug administration is to provide NO-releasing therapeutics that do not require activation by endogenous enzyme systems. Early efforts to provide NO-releasing compounds suitable for in vivo use were described in U.S. Pat. No. 4,954,526.

Diazeniumdiolates comprise a diverse class of NO-releasing compounds/materials that are known to exhibit sufficient stability to be useful as therapeutics. Although discovered more than 100 years ago by Traube et al. (*Liebigs Ann. Chem.*, 300: 81-128 (1898)), the chemistry and properties of diazeniumdiolates have been extensively reinvestigated by Keefer and co-workers, as described in U.S. Pat. Nos. 6,750,254, 6,703,046, 6,673,338, 6,610,660, 6,511,991, 6,379,660, 6,290,981, 6,270,779, 6,232,336, 6,200,558, 6,110,453, 5,910,316, 5,814,666, 5,814,565, 5,731,305, 5,721,365, 5,718,892, 5,714,511, 5,700,830, 5,691,423, 5,683,668, 5,676,963, 5,650,447, 5,632,981, 5,525,357, 5,405,919, 5,389,675, 5,366,997, 5,250,550, 5,212,204, 5,208,233, 5,185,376, 5,155,137, 5,039,705, and 4,954,526, and in Hrabie et al., *J. Org. Chem.*, 58: 1472-1476 (1993), and incorporated herein by reference.

Diazeniumdiolated compounds have been attached to polymers, substrates, and medical devices. See, for example, U.S. Pat. Nos. 6,703,046, 6,270,779, 6,673,338, 6,200,558, 6,110,453, 5,718,892, 5,691,423, 5,676,963, 5,650,447, 5,632,981, 5,525,357, and 5,405,919.

Thus, despite the extensive literature available on NO and nitric oxide-releasing compounds, there remains a need for stable nitric oxide-releasing polymers that exhibit a sustained release of nitric oxide that can be readily prepared, even from commercially available polymers. Moreover, there exists a need for a medical device, such as a stent, vascular graft, or extracorporeal blood filter, comprised of or coated with a material capable of continuously releasing NO from the first instance of blood contact to days or weeks following its first use. Such a device is useful for treating a biological disorder, such as platelet aggregation, that frequently accompanies the implantation of a medical device.

BRIEF SUMMARY OF THE INVENTION

The invention described herein provides novel nitric oxide-releasing acrylonitrile-based polymers. The polymers of the invention comprise at least two adjacent units derived from acrylonitrile monomer segments and contain at least one carbon-bound diazeniumdiolate. The diazeniumdiolated acrylonitrile-based polymers can be used in medical devices. In addition, the invention provides nitric oxide-releasing cyclic amidine compounds based on nitrile-containing compounds. In addition, the invention provides substituted or unsubstituted, nitric oxide-releasing diazeniumdiolated cyanoalkanes, wherein the cyanoalkane moiety has from about 3 to about 25 carbon atoms. The cyanoalkanes can be described generally, for example, by compounds of the formula (V), (X), and (XV) below. The substituents, $R^1$ and $R^2$, are also described below. The invention also provides compositions and medical devices comprising such diazeniumdiolated (poly)acrylonitrile derivatives and methods of using such compounds. These and other advantages of the present invention, as well as additional inventive features, will be apparent from the description of the invention provided below.

DETAILED DESCRIPTION OF THE INVENTION

Figure 1A:
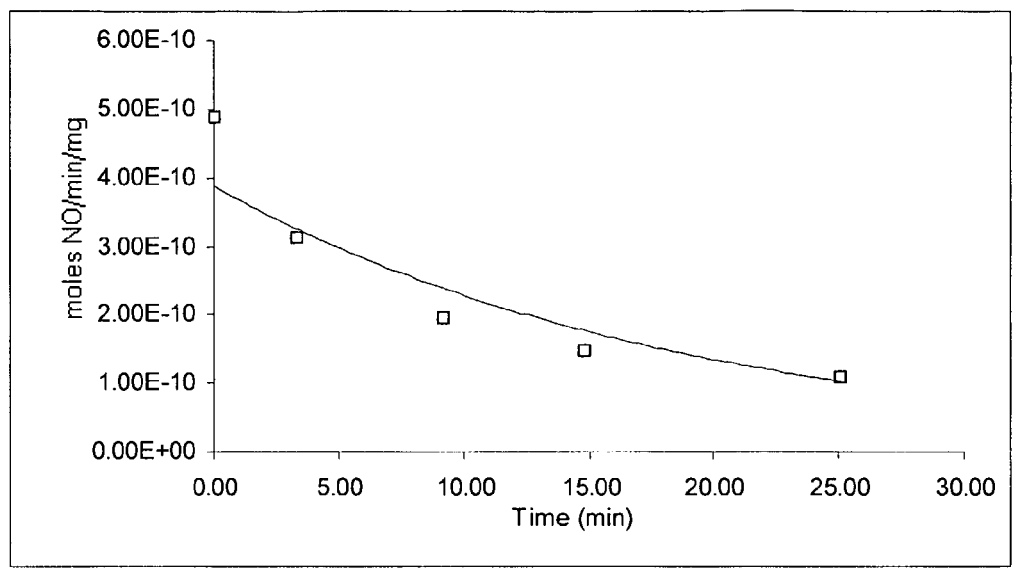
FIG. 1 is a time course of NO release from diazeniumdiolated polyacrylonitrile over (a) 30 minutes and (b) 300 minutes.

The invention provides novel acrylonitrile-based polymers comprising at least two adjacent units derived from acrylonitrile monomer and containing at least one carbon-bound diazeniumdiolate group, and which are capable of releasing nitric oxide. In addition, the invention provides nitric oxide-releasing cyclic amidine compounds based on nitrile-containing compounds and nitric oxide-releasing cyanoalkane compounds, wherein the cyanoalkane moiety has from about 3 to about 25 carbon atoms. The cyanoalkane-containing compounds (sometimes referred to as cyanoalkanes) can be described generally, for example, by compounds of formula (V), (X), and (XV) The substitutents, $R^1$ and $R^2$, are also described below. These polymers, cyclic amidine compounds, cyanoalkane compounds, and compositions and medical devices which include the polymers, cyclic amidine compounds, and cyanoalkane compounds are useful for treating biological conditions where a release of nitric oxide is beneficial.

In particular, the present invention provides a nitric oxide-releasing acrylonitrile-based polymer comprising at least two adjacent units derived from acrylonitrile and at least one nitric oxide releasing $N_2O_2^-$ group, wherein the $N_2O_2^-$ group is directly attached to a carbon atom of the polyacrylonitrile backbone. Preferably the acrylonitrile-based polymers comprise at least two adjacent units derived from acrylonitrile before exposure to nitric oxide. Because the $N_2O_2^-$ group is directly attached to a carbon atom of the polyacrylonitrile backbone, there is no need for a linking group. Preferably, when the $N_2O_2^-$ group is bonded to a carbon atom of the acrylonitrile-based polymer, the $N_2O_2^-$ group is bonded directly to the carbon that also contained the cyano substituent of the acrylonitrile subunit before exposure to NO. In keeping with the invention, the polyacrylonitrile backbone can be diazeniumdiolated with numerous $N_2O_2^-$ groups.

Typically each $N_2O_2^-$ group on the polymer also comprises a suitable counterion to balance the charge. Within a single polymer chain, the counterions can be the same or different, but preferably they are the same. Preferably, the counterion is a pharmaceutically acceptable counterion. The only requirement for the pharmaceutically acceptable counterion is biological compatibility in a mammal, such as a human. Biologically acceptable counterions include alkali metals such as sodium ion, potassium ion, lithium ion, and the like; alkaline earth metals such as magnesium ion, calcium ion, and the like; Group III metals such as aluminum ion; Group IV metals such as tin ion; and transition metals, including iron ion, copper ion, manganese ion, zinc ion, cobalt ion, vanadium ion, molybdenum ion, platinum ion, and the like. Non-metal counterions include quaternary ammonium ions and hydrogen ion. Metal ions that may be considered toxic may, nevertheless, be pharmaceutically acceptable and thus within the scope of the invention if their complexes with the diazeniumdiolates are sufficiently potent pharmacologically and the total concentration of the metal counterion upon dosing is below the toxic threshold of the metal.

The polymer comprising at least two adjacent units derived from acrylonitrile before exposure to nitric oxide can be a homopolymer of polyacrylonitrile (PAN). PAN (2) is a vinyl polymer which is prepared from acrylonitrile (1), typically via free radical vinyl polymerization. See Equation (1). PAN is often referred to as "acrylic". The arrangement of nitrile groups can be isotactic, syndiotactic, or atactic. Under free radical vinyl polymerization conditions, PAN is usually atactic. Other polymerization conditions can be used to prepare isotactic, syndiotactic, or a combination of all three configurations. In general, PAN is used to make materials such as carbon fiber. Fabrics made from polyacrylonitrile are known commercially as Orlon®, Acrilan®, and by many other trade names.

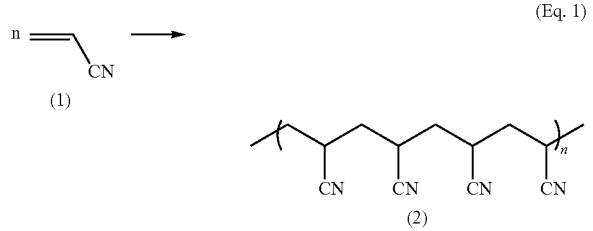

In addition, the polymer comprising at least two adjacent units derived from acrylonitrile before exposure to nitric oxide can be a copolymer with one or more different comonomers. The copolymer can comprise at least one comonomer selected from the group consisting of styrene, divinylbenzene, 4-methylstyrene, 4-chloromethylstyrene, 4-aminostyrene, 4-chlorostyrene, 4-bromostyrene, 4-vinylphenol, 4-vinylpyridine, 2-vinylpyridine, butadiene, 2-chlorobutadiene, acrylic acid, methacrylic acid, methyl methacrylate, ethyl methacrylate, acrylamide, methylacrylonitrile, ethylene, propylene, isoprene, acrolein, methacrolein, 1-glycerol methacrylate, 2-hydroxyethyl methacrylate, 2-hydroxypropyl methacrylate, vinyl alcohol, allyl alcohol, allyl acetate, vinyl acetate, allylamine, vinylamine, N-methyl vinylamine, N-methyl allylamine, N,N-dimethyl vinylamine, N,N-dimethyl allylamine, isopropenyl acetate, tetrafluoroethylene, chlorotrifluoroethylene, dichloroethylene, vinylidene difluoride, vinylchloride, N-vinylpyrrolidone, ethylenimine, ethyleneglycol, ethylene oxide, tetrahydrofuran, glycidyl acrylate, glycidyl methacrylate, lactate, glycolate, urethane, combinations, and mixtures thereof. Other suitable comonomers are described in U.S. Pat. Nos. 5,405,919, 5,525,357, 5,632,981, 5,650,447, 5,676,963, 5,691,423, and 5,718,892, and are incorporated herein by reference. Preferably, the copolymer comprises butadiene and/or styrene as comonomers in addition to at a monomer with least two adjacent units derived from acrylonitrile.

Copolymers of PAN are commercially used to make fabric for knitted clothing and outdoor fabrics (e.g., tents). Copolymers of PAN and vinyl chloride are flame-retardant and used as modacrylic fibers. Poly(butadiene-co-acrylonitrile) (BUNA-N) is a rubber. In addition, copolymers poly(styrene-co-acrylonitrile) (SAN) and poly(acrylonitrile-co-butadiene-co-styrene) (ABS) are used as plastics. Polyacrylonitrile is also used in resins when the polyacrylonitrile is terminated with a functional group, such as vinyl, carboxy, primary amine, secondary amine, and hydroxyl.

The comonomers can be present in any suitable ratio in the copolymer. For example, if two monomers, A and B, are used, the resulting copolymer can have a range of weight ratios of A:B, including from about 99:1 to about 1:99. For example, the copolymer can have weight ratios of at least 25:75, at least 50:50, at least 75:25, at least 20:80, at least 30:70, at least 40:60, at least 60:40, at least 70:30, or at least 80:20. The copolymers can be block copolymers, graft copolymers, alternating, or random copolymers. Preferably, they are random copolymers.

In addition, the present invention encompasses polymer blends, in which two or more polymers are physically combined but not chemically linked. Any of the foregoing polymers and nylon polymers are suitable for use as a blend with an NO-releasing polymer comprising at least two adjacent units of acrylonitrile before exposure to nitric oxide. The only requirement for preparing a polymer blend is that the polymers are miscible with one another.

Many polymers and copolymers comprising at least two adjacent units derived from acrylonitrile monomer are commercially available, typically in the form of a powder, pellets, beads, granules, fiber, film, sheet, or fabric. Alternatively, suitable polymers and copolymers can be synthetically prepared using standard techniques. For example, a polymer comprising at least two adjacent units derived from acrylonitrile monomer can be prepared using free radical polymerization, anionic polymerization, cationic polymerization, Ziegler-Natta catalysis, or metallocene catalysis. Polymer materials of the present invention can take any suitable form, such as a fiber, fabric, membrane, film, gel, coating, rubber, plastic, or matrix. Typically, the desired form of the polymer or copolymer and/or the desired molecular weight will dictate the polymerization conditions to be used.

The polymers and copolymers, either before or after reaction with NO, can be characterized quantitatively using known methods. For example, molecular weight determinations can be made using gel permeation chromatography (also known as size exclusion chromatography and gel filtration chromatography), matrix-assisted laser desorption/ionization mass spectroscopy (MALDI), light scattering (e.g., low angle and multi angle), small angle neutron scattering (SANS), sedimentation velocity, end group analysis, osmometry, cryoscopy/ebulliometry, and viscometry.

Also, further structural characterization of the polymer can be accomplished using, for example, both solution and solid state nuclear magnetic resonance spectroscopy (NMR), infrared spectroscopy (IR), ultraviolet spectroscopy (UV-vis), differential scanning calorimetry (DSC), and mass spectrometry. Nitric oxide detection can be determined using known techniques such as those described in U.S. Pat. Nos. 6,511, 991 and 6,379,660; Keefer, et al., "NONOates(1-Substituted Diazen-1-ium-1,2 diolates) as Nitric Oxide Donors: Convenient Nitric Oxide Dosage Forms," *Methods in Enzymology*, 28: 281-293 (1996); Horstmann et al., "Release of nitric oxide from novel diazeniumdiolates monitored by laser magnetic resonance spectroscopy," *Nitric Oxide*, 6(2): 135-41 (2002); and Kitamura et al., "In vivo nitric oxide measurements using a microcoaxial electrode," *Methods Mol. Biol.*, 279: 35-44 (2004), which are incorporated herein by reference. In general, the amount of NO produced can be detected by a chemiluminescence method, electrochemical method, absorbance method, and/or the Griess assay (Schmidt et al., In Methods in Nitric Oxide Research; Feelisch, M.; Stamler, J., Eds.; "Determination of nitrite and nitrate by the Griess reaction." John Wiley and Sons, Ltd.: New York; 1996; pp. 491-497). In addition, nitric oxide assay kits are commercially available.

When an acrylonitrile-based polymer comprising at least two adjacent units derived from acrylonitrile is reacted with nitric oxide in the presence of a base, preferably a strong base, a diazeniumdiolated polymer forms that is capable of releasing nitric oxide over an extended period of time. The release of nitric oxide can be either in vivo or ex vivo, depending on the ultimate use of the polymer. Preferably, the polymer releases nitric oxide at its intended site for treatment of a biological disorder. Accordingly, the present invention provides a method of releasing nitric oxide from a nitric oxide-releasing acrylonitrile-based polymer comprising at least two adjacent units of acrylonitrile and at least one nitric oxide releasing $N_2O_2^-$ group, wherein the $N_2O_2^-$ group is attached directly to a carbon atom, preferably to a carbon atom on the polyacrylonitrile backbone. Preferably, the release of NO is under physiological conditions. In one example, the release of NO can occur in vivo or ex vivo at about 37° C. and pH about 7. Also, preferably a polymer of the present invention releases NO over a period of at least one day (i.e., at least about 24 hours), more preferably at least three days (i.e., at least about 72 hours), more preferably at least 5 days (i.e., at least about 120 hours), and most preferably at least 7 days (i.e., at least about 168 hours).

In order to prepare a diazeniumdiolated polymer of the present invention, a nucleophile, such as a strong base, is used to initiate the reaction. In general, nitric oxide (NO) releasing materials derived, at least in part, from acrylonitrile can be prepared as follows: A solution or slurry, as appropriate, of the desired nitrile-containing polymer is prepared in a solution of strong base in a solvent contained in a Parr pressure bottle. Nitrogen, argon, or other inert gas is passed through the apparatus and bubbled through the solution for a time sufficient to create an inert environment. The bottle is placed into the reactor system (see, for example, Hrabie et al., *J. Org. Chem.*, 58: 1472 (1993)), further flushed with inert gas, vented, and nitric oxide gas is admitted to a pressure suitable for reacting with the starting material. The reaction is stirred for a time sufficient to allow the reaction to go to completion at room temperature with the addition of NO as needed to maintain the reservoir pressure. Excess NO is then vented, and inert gas is bubbled through the resultant slurry for several minutes. The product is isolated by filtration, washed with solvent (e.g., methanol and ethyl ether), and dried in vacuo for several hours or overnight, as appropriate. The products typically are stored in glass jars in a refrigerator until required for experimentation.

Any suitable base can be used; a suitable base is considered a base that can initiate the reaction without itself reacting directly with NO. Preferably, the base is a metal alkoxide of the formula MOR, wherein M is the cation discussed above, and R is an unsubstituted or substituted $C_{1-12}$ straight chain alkyl, or an unsubstituted or substituted $C_{3-12}$ branched chain alkyl, a phenyl, naphthyl, or $C_{1-12}$ trialkylsilyl. Preferably R is methyl, more preferably R is trimethylsilyl. Specific bases that can be used include sodium methoxide, potassium isopropoxide, sodium t-butoxide, potassium t-butoxide, lithium trimethylsilanoate, sodium trimethylsilanoate, and potassium trimethylsilanoate. Furthermore, sodium hydroxide is a suitable base for initiating the reaction. For example, sodium hydroxide can be used to initiate the reaction using either an aqueous solution or as a suspension in a suitable organic solvent.

While not wishing to be bound by any theory, it is believed that in the presence of a base, adjacent acrylonitrile units form an amidine which then further reacts with nitric oxide. See, for example, Equation (2). It is believed that multiple ring structures are possible along the polymer backbone depending on the number and conformation of acrylonitrile units. One skilled in the art will also recognize the theoretical possibility that some NO can be sequestered in these polymers by electrostatic interaction with the pi electrons contained in the multiple bonds (i.e., to form clathrate-type or sandwich-like structures), or that the NO may react via different mechanisms (via extraction of the alpha proton from the original nitrile, for example). Indeed, to some extent, these and other possible structures may exist in the materials of the present invention.

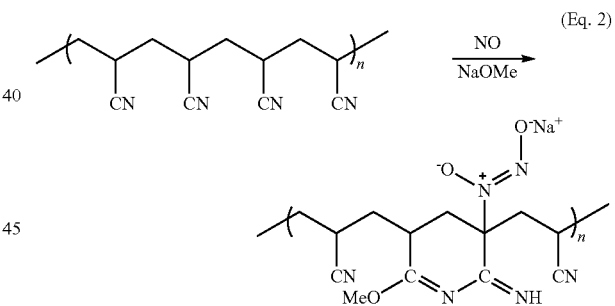

(Eq. 2)

In addition to providing NO-releasing polymers, the present invention provides NO-releasing cyclic amidines derived from nitrile-containing compounds, and substituted or unsubstituted, NO-releasing diazeniumdiolated cyanoalkanes. For example, the substituted or unsubstituted, NO-releasing diazeniumdiolated cyanoalkane-containing compounds can be formed from the NO-releasing cyclic amidine compounds. As described herein, the NO-releasing cyclic amidine compounds of the present invention can undergo a ring opening reaction to produce the corresponding NO-releasing cyanoalkane compounds. By way of illustration, when the NO-releasing cyclic amidine compounds of the present invention are treated with a suitable solvent, such as aqueous methanol or acetone, a NO-releasing cyanoalkane can be formed. Generally, the resulting cyanoalkane-containing compound has the same substitution as the cyclic amidine from which it is formed, although those skilled in the art will appreciate that other chemical modifications can be made to the compound. In addition, the present invention provides NO-releasing compounds comprising both cyclic amidine and cyanoalkane moieties. For example, NO-releasing compounds comprising both cyclic amidine and cyanoalkane moieties can be formed from NO-releasing cyclic amidine compounds which undergo partial ring opening reactions.

As previously described for the NO-releasing acrylonitrile polymers, the NO-releasing cyclic amidine and cyanoalkane-containing compounds comprise at least one NO-releasing $N_2O_2^-$ group, including a suitable counterion, wherein the $N_2O_2^-$ group is directly attached to a carbon atom. Because the $N_2O_2^-$ group is directly attached to a carbon atom, there is no need for a linking group. Preferably, the $N_2O_2^-$ group is bonded directly to the carbon atom or atoms to which is bonded the cyano substituent of the acrylonitrile subunit before exposure to NO. In keeping with the invention, the NO-releasing cyclic amidine and cyanoalkane compounds can be diazeniumdiolated with numerous $N_2O_2^-$ groups.

Accordingly, the present invention provides NO-releasing compounds of the formula (I),

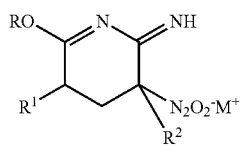

wherein $R^1$ and $R^2$ are the same or different and each is unsubstituted or substituted $C_{1-12}$ straight chain alkyl, an unsubstituted or substituted $C_{3-12}$ branched chain alkyl, an unsubstituted or substituted $C_{2-12}$ straight chain alkenyl, an unsubstituted or substituted $C_{3-12}$ branched chain alkenyl, an unsubstituted or substituted $C_{3-8}$ cycloalkyl, an unsubstituted or substituted $C_{1-12}$ alkoxy, nitrile, halo, an unsubstituted or substituted benzyl, an unsubstituted or substituted aryl, an unsubstituted or substituted piperazino, an unsubstituted or substituted morpholinyl, amino, an unsubstituted or substituted $C_{1-12}$ alkylamino, an unsubstituted or substituted $C_{6-30}$ arylamino, an unsubstituted or substituted $C_{1-12}$ dialkylamino, an unsubstituted or substituted $C_{6-30}$ diarylamino, carboxy-$C_{1-12}$ alkylamino, carboxy-$C_{1-12}$ dialkylamino, an unsubstituted or substituted acetoxy, carboxy, an unsubstituted or substituted carboxyethyl, an unsubstituted or substituted $C_{1-12}$ alkylcarbonyl, thio, an unsubstituted or substituted $C_{1-12}$ alkylthio, an unsubstituted or substituted $C_{1-12}$ alkyloxy, carboxamido, an unsubstituted or substituted $C_{1-12}$ alkylcarboxamido, an unsubstituted or substituted $C_{1-12}$ dialkylcarboxamido, an unsubstituted or substituted phenoxy, an unsubstituted or substituted benzyloxy, phenylcarbonyl, benzylcarbonyl, an unsubstituted or substituted nitrophenyl, $C_{1-12}$ trialkylsilyl or nitro; R is an unsubstituted or substituted $C_{1-12}$ straight chain alkyl, an unsubstituted or substituted $C_{3-12}$ branched chain alkyl, a phenyl, naphthyl or $C_{1-12}$ trialkylsilyl; and M is a counterion as described herein. Preferably, $R^1$ and/or $R^2$ is hydrogen, $C_{1-12}$ straight chain alkyl, $C_{3-12}$ branched chain alkyl, an unsubstituted or substituted $C_{3-8}$ cycloalkyl, or aryl. More preferably, $R^1$ and/or $R^2$ is hydrogen or $C_{1-12}$ straight chain alkyl, such as methyl.

The present invention also provides NO-releasing compounds of formula (II),

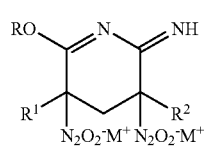

wherein $R^1$, $R^2$, R, and M are as described above. For example, further reaction of a compound of formula (I) with NO produces a compound of formula (II). Compounds of formula (I) and (II) can undergo hydrolysis to form NO-releasing compounds of formula (III) and (IV), respectively, wherein $R^1$, $R^2$, and M are as described above.

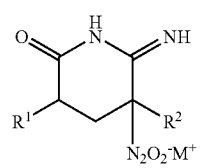

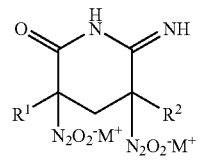

For example, when a compound of formula (II) is dissolved in a mixture of methanol and water, a compound of formula (IV) can be isolated.

The present invention further provides NO-releasing compounds of the formula (V),

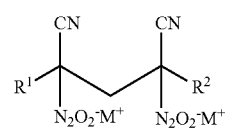

wherein $R^1$, $R^2$, and M are the same as described above. For example, a compound of formula (IV) can undergo ring opening to produce the cyano compound of formula (V). By way of illustration, when a compound of formula (IV) is dissolved in a mixture of methanol and water, a compound of formula (V) can be isolated.

The present invention also provides NO-releasing compounds of the formula (VI),

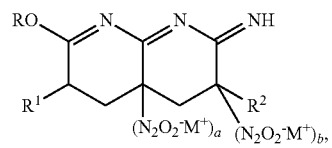

wherein $R^1$, $R^2$, R, and M are as described above; and a is 0 or 1 and b is 0 or 1. Preferably, $R^1$ and/or $R^2$ is hydrogen, $C_{1-12}$ straight chain alkyl, $C_{3-12}$ branched chain alkyl, an unsubstituted or substituted $C_{3-8}$ cycloalkyl, or aryl. More preferably, $R^1$ and/or $R^2$ is hydrogen or $C_{1-12}$ straight chain alkyl, such as methyl.

The present invention further provides NO-releasing compounds of the formula (VII),

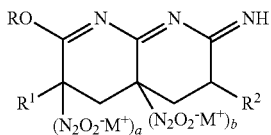

(VII)

wherein $R^1$, $R^2$, R, M, a, and b are as described above. Compounds of formula (VI) and (VII) can be hydrolyzed to produce compounds of formula (VIII) and (IX), respectively.

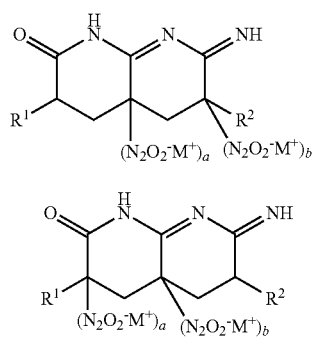

(VIII)

(IX)

wherein $R^1$, $R^2$, M, a, and b are as described above. For example, when a compound of formula (VII) is treated with aqueous acetone, a compound of formula (IX) can be formed.

The present invention also provides NO-releasing compounds of the formula (X),

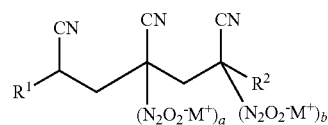

(X)

wherein $R^1$, $R^2$, M, a, and b are as described above. A compound of formula (IX) can undergo ring opening to produce a compound of formula (X). For example, when a compound of formula (IX) is treated with aqueous acetone a compound of formula (X) is isolated.

The present invention also provides NO-releasing compounds of the formula (XI),

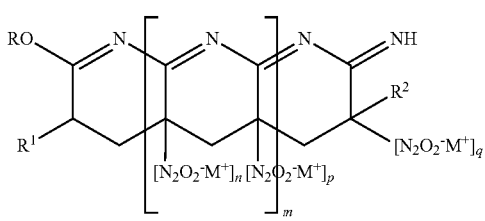

(XI)

wherein $R^1$, $R^2$, R, and M are as described above; m is 1-7; n is 0 or 1; p is 0 or 1; and q is 0 or 1. Preferably, $R^1$ and/or $R^2$ is hydrogen, $C_{1-12}$ straight chain alkyl, $C_{3-12}$ branched chain alkyl, an unsubstituted or substituted $C_{3-8}$ cycloalkyl, or aryl. More preferably, $R^1$ and/or $R^2$ is hydrogen or $C_{1-12}$ straight chain alkyl, such as methyl. Preferably m is 1. Preferably n is 0 and p is 1.

The present invention further provides NO-releasing compounds of the formula (XII),

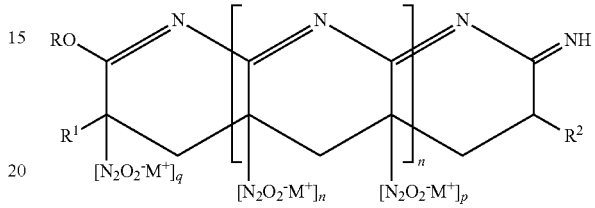

wherein $R^1$, $R^2$, R, M, m, n, p, and q are as described above.

Further, the present invention provides NO-releasing compounds of the formula (XIII) and (XIV),

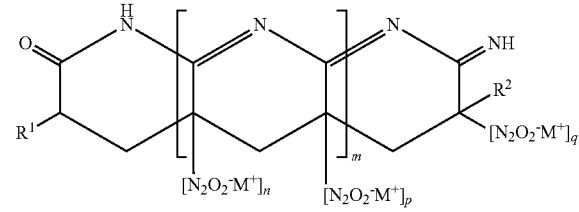

(XIII)

(XIV)

wherein $R^1$, $R^2$, M, m, n, p, and q are as described above.

The present invention also provides NO-releasing compounds of the formula (XV),

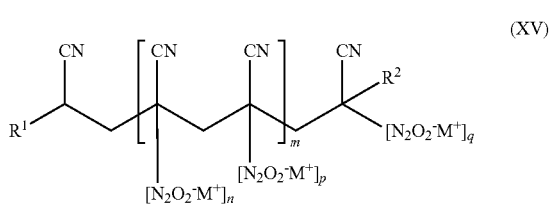

(XV)

wherein $R^1$, $R^2$, M, m, n, p, and q are as described above.

The present invention also provides NO-releasing compounds of the formula (XVI),

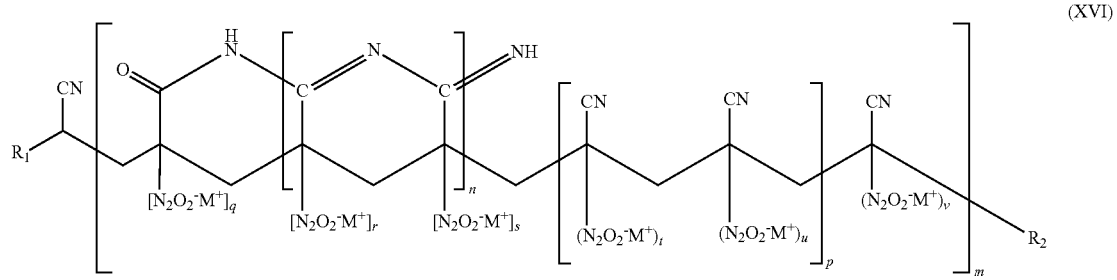

wherein $R^1$, $R^2$, and M are as described above; m is 1-7; n is 1-7; p is 1-7; q is 0 or 1; r is 0 or 1; r is 0 or 1; s is 0 or 1; t is 0 or 1; u is 0 or 1; and v is 0 or 1.

Any one or more of $R^1$, $R^2$, and R of formula (I)-(XVI) can be optionally substituted. Generally each of $R^1$, $R^2$, and R can have 1 to 10 substituents (e.g., 1 to 8, 1 to 6, 1 to 4, 1 to 3 substituents) that are independently selected from the group consisting of $C_{1-12}$ alkyl, $C_{6-30}$ aryl, $C_{1-12}$ alkoxy, $C_{1-12}$ aryloxy, benzyl, benzyloxy, $C_{6-30}$ arylamino, $C_{6-30}$ diarylamino, nitrile, tolyl, xylyl, mesityl, anisyl, pyrrolidinyl, dioxanyl, $C_{1-12}$ alkylthio, $C_{5-30}$ heteroaryl, such as pyranyl, pyrrolyl, furanyl, thiophenyl, thiazolyl, pyrazolyl, pyridinyl, or pyrimidinyl, phenylcarbonyl, nitrophenyl, $C_{1-12}$ trialkylsilyl, $C_{1-12}$ trialkylammonium, tetrahydrofuranyl, tetrahydropyranyl, piperidinyl, morpholinyl, halo, cyano, hydroxy, thio, $C_{3-8}$ cycloalkyl, amino, $C_{1-12}$ alkylamino, and $C_{1-12}$ dialkylamino.

In another aspect, the invention provides a composition, including a pharmaceutical composition, comprising at least one novel diazeniumdiolated acrylonitrile-containing polymer and/or a compound of formula (I)-(XVI). Preferably, the pharmaceutical composition further comprises a pharmaceutically acceptable carrier.

One skilled in the art will appreciate that suitable methods of administering a composition comprising at least one compound of formula (I)-(XVI) to a mammal, e.g., a mammal such as a human, are known, and, although more than one route can be used to administer a particular composition, a particular route can provide a more immediate and more effective reaction than another route. Pharmaceutically acceptable carriers are also well known to those who are skilled in the art. The choice of carrier will be determined, in part, both by the particular composition and by the particular method used to administer the composition. Accordingly, there are a wide variety of suitable formulations of the pharmaceutical composition of the present invention.

Formulations suitable for oral, inhalation, or parenteral administration preferably comprise at least one compound of formula (I)-(XVI). Formulations suitable for oral administration can consist of (a) liquid solutions, such as an effective amount of the diazeniumdiolated polymer dissolved in diluents, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The diazeniumdiolated polyacrylonitriles of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a mammal, particularly a human, in the context of the present invention should be sufficient to effect a therapeutic response in the mammal over a reasonable time frame. The dose will be determined by the strength of the particular compositions employed (taking into consideration, at least, the rate of NO evolution, the extent of NO evolution, and the bioactivity of any decomposition products derived from the diazeniumdiolates) and the condition of the mammal (e.g., human), as well as the body weight of the mammal (e.g., human) to be treated. The size of the dose also will be determined by the existence, nature, and extent of any adverse side effects that might accompany the administration of a particular composition. A suitable dosage for internal administration is 0.01 to 100 mg/kg per day. A preferred dosage is 0.01 to 35 mg/kg per day. A more preferred dosage is 0.05 to 5 mg/kg per day. A suitable concentration in pharmaceutical compositions for topical administration is 0.05 to 15% (by weight). A preferred concentration is from 0.02 to 5%. A more preferred concentration is from 0.1 to 3%.

A nitric oxide-releasing acrylonitrile-based polymer of the present invention can be bound to a substrate. The diazeniumdiolated polymer can be contacted with a substrate, in which, preferably, the substrate has moieties that allow for chemical bonding of the nitric oxide-releasing polymer. See, for example, U.S. Pat. Nos. 6,703,046, 6,528,107, and 6,270,779, which are incorporated herein in their entirety. Alternatively, a compound of formula (I)-(XVI) can be contacted with a substrate and subsequently bound thereto.

The substrate can be of any suitable biocompatible material, such as metal, glass, ceramic, plastic, or rubber. Preferably, the substrate is metal. The substrate used in the preparation of the medical device can be derived from any suitable form of a biocompatible material, such as, for example, a sheet, a fiber, a tube, a fabric, an amorphous solid, an aggregate, dust, or the like.

Metal substrates suitable for use in the invention include, for example, stainless steel, nickel, titanium, tantalum, aluminum, copper, gold, silver, platinum, zinc, Nitinol, inconel, iridium, tungsten, silicon, magnesium, tin, alloys, coatings containing any of the above, and combinations of any of the above. Also included are such metal substrates as galvanized steel, hot dipped galvanized steel, electrogalvanized steel, annealed hot dipped galvanized steel, and the like. Preferably, the metal substrate is stainless steel.

Glass substrates suitable for use in the invention include, for example, soda lime glass, strontium glass, borosilicate glass, barium glass, glass-ceramics containing lanthanum as well as combinations thereof.

Ceramic substrates suitable for use in the invention include, for example, boron nitrides, silicon nitrides, aluminas, silicas, combinations thereof, and the like.

Plastic substrates suitable for use in the invention include, for example, acrylics, acrylonitrile-butadiene-styrene, acetals, polyphenylene oxides, polyimides, polystyrene, polypropylene, polyethylene, polytetrafluoroethylene, polyvinylidene, polyethylenimine, polyesters, polyethers, polyamide, polyorthoester, polyanhydride, polyether sulfone, polycaprolactone, polyhydroxy-butyrate valerate, polylactones, polyurethanes, polycarbonates, polyethylene terephthalate, as well as copolymers and combinations thereof. Typical rubber substrates suitable for use in the invention include, for example, silicones, fluorosilicones, nitrile rubbers, silicone rubbers, fluorosilicone rubbers, polyisoprenes, sulfur-cured rubbers, butadiene-acrylonitrile rubbers, isoprene-acrylonitrile rubbers, and the like. The substrate could also be a protein, an extracellular matrix component, collagen, fibrin or another biologic agent or a mixture thereof. Silicones, fluorosilicones, polyurethanes, polycarbonates, polylactones, and mixtures or copolymers thereof are preferred plastic or rubber substrates because of their proven bio- and hemocompatability when in direct contact with tissue, blood, blood components, or bodily fluids.

Other suitable substrates include those described in WO 00/63462 and U.S. Pat. No. 6,096,070, and incorporated herein by reference.

The invention provides medical devices which are capable of releasing nitric oxide when in use, but which are otherwise inert to nitric oxide release. In particular, NO-releasing functional groups are bound to an acrylonitrile-based polymer comprising at least two adjacent units of acrylonitrile with at least one carbon-bound diazeniumdiolate group which, in turn, is coated on a substrate. Alternatively, the diazeniumdiolated acrylonitrile-containing polymer can form the medical device itself.

A "medical device" includes any device having surfaces that contact tissue, blood, or other bodily fluids in the course of their use or operation, which are found on or are subsequently used within a mammal. Medical devices include, for example, extracorporeal devices for use in surgery, such as blood oxygenators, blood pumps, blood storage bags, blood collection tubes, blood filters including filtration media, dialysis membranes, tubing used to carry blood and the like which contact blood which is then returned to the patient or mammal. Medical devices also include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include penile implants, condoms, tampons, sanitary napkins, ocular lenses, sling materials, sutures, hemostats used in surgery, antimicrobial materials, surgical mesh, transdermal patches, and wound dressings/bandages.

Since nitric oxide has been shown to inhibit platelet aggregation (e.g., WO 93/05773), the nitric oxide-releasing polymer of the invention is useful in laboratory and medical applications and procedures that involve contact with blood. The NO-releasing polymeric material can be used in vivo, for example, to line or form blood-contacting surfaces of an in-dwelling device such as a pacemaker, an implantable pulse generator (IPG), an implantable cardiac defibrillator (ICD), a pacemaker cardioverter defibrillator (PCD), a defibrillator, a spinal stimulator, a brain stimulator, a sacral nerve stimulator, a stent, a catheter, a lead, or a chemical sensor. Examples of chemical sensors include optical or electrochemical sensors that can continuously monitor or measure physiologically important ions ($H^+$, $K^+$, $Na^+$, etc.) and gases, such as $CO_2$ and $O_2$, in the blood. Ex vivo applications include incorporation of the nitric oxide releasing polymeric material into the blood-contacting surfaces of extracorporeal sensors and circulation devices such as blood oxygenators.

For example, extracorporeal membrane oxygenation (ECMO) is a means in which blood is oxygenated outside the body. ECMO takes over the work of the lungs and is often used for newborn babies whose lungs are failing despite other treatments. The procedure involves inserting plastic tubes called cannulae into the vein and artery of the neck and/or groin. The anticoagulant heparin is given to patients on ECMO to prevent clotting in the ECMO tubing and/or the development of clots on the membrane which could break off and migrate to the lungs or brain. The most common side effect of heparin is bleeding. Accordingly, the nitric oxide-releasing polymer of the present invention has utility in combination with or as a substitute for heparin coatings and/or infusions to reduce or inhibit platelet aggregation or adherence. Similar problems with clotting of membranes and filters used in dialysis procedures can be solved by constructing these materials from the polymers of the present invention.

Medical sutures typically are made from synthetic polymers such as nylon, polytetrafluoroethylene, polyester, polyethylene, polypropylene, polyglycolic acid, or polyglactin 910 and can be monofilament or many filaments twisted together, spun together, or braided. Sutures used internally, such as those used to mend an artery, are used either to approximate and maintain tissues until the natural healing process has provided a sufficient level of wound strength or to compress blood vessels in order to stop bleeding. The blood must clot enough to begin healing the wound, however, the blood platelets must continue to be able to flow through the tissue (e.g., artery) and not result in a blockage. Thus, an embodiment of the present invention is a suture filament that can be coated with an NO-releasing polymer of the present invention such that the wound is closed, yet the local release of NO can prevent or reduce platelet aggregation, thereby preventing or minimizing a blockage. Alternatively, an NO-releasing acrylonitrile-based polymer comprising at least two adjacent acrylonitrile units can be copolymerized with any suitable comonomer (e.g., propylene) to prepare an NO-releasing copolymer that can be used as a suture filament. Also, suture thread (e.g., nylon) could be twisted, spun, or braided together with a nitric oxide-releasing polymer or copolymer of the present invention to prepare a multifilament suture. The only requirements are that the resulting suture thread maintains the desired level of NO release, strength, elasticity, and non-reactivity with bodily tissue.

A vascular graft is a tissue graft involving the implantation or transplantation of vascular tissue. The use of vascular grafts is a common practice to replace a damaged artery or to create a new artery to improve blood flow. While autologous vessels are preferable, over 30% of patients are not able to provide biological vessels, making synthetic grafts the only alternative (Bellingham et al., Biochim. et Biophys. Acta-Prot. Struct. Mol. Enz., 1550(1): 6-19 (2001)). The most common synthetic vascular graft materials are expanded polytetrafluoroethylene (ePTFE) (e.g., Gore-Tex®) and polyester (e.g., Dacron®). Dacron® grafts have recently been manufactured coated with protein (e.g., collagen/albumin) to reduce blood loss and antibiotics (e.g., ciprofloxacin) to prevent graft infection. See, for example, Ozaki et al., J. Surg. Res., 55(5): 543-7 (1993) and Phaneuf et al., J. Biomed. Mater. Res., 27(2): 233-7 (1993). An embodiment of the present invention is to coat a polymeric vascular graft with a diazeniumdiolated acrylonitrile-based polymer, such that the graft can release NO locally to inhibit platelet aggregation and promote blood flow. Alternatively, the graft itself could be prepared from an NO-releasing polymer or copolymer of the present invention.

Nitric oxide-releasing acrylonitrile-based polymers comprising at least two adjacent units of acrylonitrile are useful for the treatment of many biological disorders. The present invention provides methods of using a nitric oxide-releasing acrylonitrile-based polymer of the invention. In one embodiment, a method of treating a mammal, e.g., a human, with a biological disorder treatable with nitric oxide, is provided. The method comprises administering to the mammal (e.g., human), in need thereof a diazeniumdiolated polymer comprising at least two adjacent units of acrylonitrile before exposure to nitric oxide, a composition thereof, or a polymer-containing medical device in an amount sufficient to treat the biological disorder in the mammal (e.g., human). Preferably, the method for treating a biological disorder in a mammal in which dosage with nitric oxide is beneficial, comprises administering to a specific location on or within the mammal a medical device comprising a nitric oxide-releasing acrylonitrile-based polymer comprising at least two adjacent units of acrylonitrile and at least one nitric oxide releasing $N_2O_2^-$ group, wherein the $N_2O_2^-$ group is attached directly to a carbon atom in the polyacrylonitrile backbone, in an amount sufficient to release a therapeutically effective amount of nitric oxide. The treatment can be prophylactic or therapeutic. By "prophylactic" is meant any degree in inhibition of the onset of the biological disorder, including complete inhibition. By "therapeutic" is meant any degree in inhibition of the progression of the biological disorder in the mammal (e.g., human).

In these embodiments, "biological disorder" can be any biological disorder, so long as the disorder is treatable with nitric oxide. Suitable biological disorders include hypertension, restenosis, cancer, impotency, platelet aggregation, and a biological disorder due to a genetic defect or infection with an infectious agent, such as a virus, bacterium, fungus or parasite. Moreover, polymers of the present invention can be used to promote the growth of new blood vessels and capillaries in a process known as angiogenesis. The NO-releasing polymers of the present invention may also be used to reduce inflammation and promote healing when used as a coating or substrate for implantable medical devices.

The present invention provides a method for promoting angiogenesis in a tissue of a mammal in need thereof. The method comprises either applying or administering to the mammal a medical device comprising a nitric oxide-releasing polymer comprising at least two adjacent units of acrylonitrile before exposure to nitric oxide and at least one nitric oxide releasing $N_2O_2^-$ group, wherein the $N_2O_2^-$ group is attached directly to a carbon atom in the polyacrylonitrile backbone, to a specific location on or within the mammal in an amount effective to promote angiogenesis in the tissue. Conditions that can be treated in accordance with this method of the invention are characterized by insufficient vascularization (or predisposition thereto) of the affected tissue, i.e., conditions in which neovascularization is needed to achieve sufficient vascularization in the affected tissue, and include, for example, diabetic ulcers, gangrene, surgical or other wounds requiring neovascularization to facilitate healing; Buerger's syndrome; hypertension; ischemic diseases including, for example, cerebrovascular ischemia, renal ischemia, pulmonary ischemia, limb ischemia, ischemic cardiomyopathy, myocardial ischemia, ischemia of tissues such as, for example, muscle, brain, kidney and lung; and other conditions characterized by a reduction in microvasculature. Exemplary tissues in which angiogenesis can be promoted include: hypertension; ulcers (e.g., diabetic ulcers); surgical wounds; ischemic tissue, i.e., a tissue having a deficiency in blood as the result of an ischemic disease including, for example, muscle, brain, kidney and lung; ischemic diseases including, for example, cerebrovascular ischemia, renal ischemia, pulmonary ischemia, limb ischemia, ischemic cardiomyopathy, and myocardial ischemia.

The following examples further illustrate the invention but, of course, should not be construed as in any way limiting its scope.

Example 1

This example describes the preparation of a nitric oxide (NO) releasing polyacrylonitrile.

A solution of sodium methoxide in methanol was prepared by adding 100 mL of a commercially-obtained 25% sodium methoxide in methanol solution (Aldrich) to 100 mL of anhydrous methanol contained in a 500 mL glass Parr hydrogenation bottle. To this was added 20.0 g finely powdered polyacrylonitrile (Aldrich), and the resulting slurry was treated with NO for 20 h, as described above. Yield: 19.2 g, light yellow-brown to tan powder.

Example 2

This example describes the preparation of a nitric oxide (NO) releasing SAN copolymer.

A solution of 10.0 g poly(styrene-co-acrylonitrile) containing 25% acrylonitrile by weight (Polysciences, Inc.) in 100 mL anhydrous tetrahydrofuran (THF) was prepared in a 500 mL glass Parr hydrogenation bottle, and to this was added 25 mL of a 1.0 M solution of sodium trimethylsilanoate in THF (Aldrich). The resulting solution was treated with NO for 20 h, then poured into 1 L of methanol to reprecipitate the polymer. The solvent was decanted, and the large off white clumps were washed with methanol and dried in vacuo. Yield: 9.72 g, off white powdery clumps.

Example 3

This example describes the preparation of a nitric oxide (NO) releasing BUNA-N copolymer.

A solution of 11 g amine-terminated poly(acrylonitrile-co-butadiene) containing 18% acrylonitrile by weight (Aldrich Cat. No. 41, 890-0; contains aminoethyl piperazine groups bonded at the ends of the polymer chains to achieve an amine E.W. of 900; CA Registry No. 68683-29-4) in 200 mL anhydrous THF was prepared in a 500 mL glass Parr hydrogenation bottle, and to this was added 10 mL of a 25% solution of sodium methoxide in methanol. The resulting solution was treated with NO for 18 h, and the resulting gelatinous material was poured into 1 L methanol to produce a light rubbery precipitate, which was isolated by decanting the liquid, rinsing with methanol, squeezing dry, and drying in vacuo. Yield: 8.4 g, rubbery tan solid.

Example 4

This example describes the preparation of a nitric oxide (NO) releasing BUNA-N rubber exam glove.

A solution of sodium methoxide in methanol was prepared by mixing 25 mL 25% sodium methoxide in methanol with 100 mL anhydrous methanol in a large glass Parr hydrogenation bottle. Several approximately square pieces were cut from a powder-free nitrile rubber exam glove (Kimberly-Clark No. 50601) to give an approximate weight of 1 g of pieces which were then added to the solution. This slurry was treated with NO for 48 h, after which the BUNA-N rubber pieces were rinsed with methanol and dried in vacuo.

Example 5

This example describes the preparation of a nitric oxide (NO) releasing acrylic fiber.

A solution of sodium methoxide in methanol was prepared by mixing 25 mL 25% sodium methoxide in methanol with 100 mL anhydrous methanol in a large glass Parr hydrogenation bottle. Several lengths of white yarn were cut from a sweater labeled as 100% acrylic to give an approximate weight of 1 g of pieces, which were then added to the solution. This mixture was treated with NO for 72 h, after which the slightly off white pieces were removed with tweezers, rinsed with methanol, and dried in vacuo.

Example 6

This example describes the preparation of a nitric oxide (NO) releasing poly(propylene-co-acrylonitrile) copolymer.

A solution of sodium methoxide in methanol was prepared by mixing 25 mL 25% sodium methoxide in methanol with 100 mL anhydrous methanol in a large glass Parr hydrogenation bottle. Several lengths of light grey yarn were cut from the lining of a jacket labeled as poly(propylene-co-acrylonitrile) containing 73% acrylonitrile to give an approximate weight of 1 g of pieces, which were then added to the solution. This mixture was treated with NO for 72 h, after which the still grey pieces were removed with tweezers, rinsed with methanol, and dried in vacuo.

Example 7

This example describes the preparation of nitric oxide (NO) releasing PAN hollow fibers from a blood filter.

A solution of sodium methoxide in methanol was prepared by mixing 25 mL 25% sodium methoxide in methanol with 175 mL anhydrous methanol in a large glass Parr hydrogenation bottle. Several polyacrylonitrile hollow fibers were removed from an Asahi PAN-03 hemofilter (Asahi Medical Co., Ltd.), immersed in this solution, and treated with NO for 21 h. The pale yellow/orange fibers were removed with tweezers, washed with methanol, and dried in vacuo.

Example 8

This example describes the release of NO from diazeniumdiolated PAN.

Figure 1B:
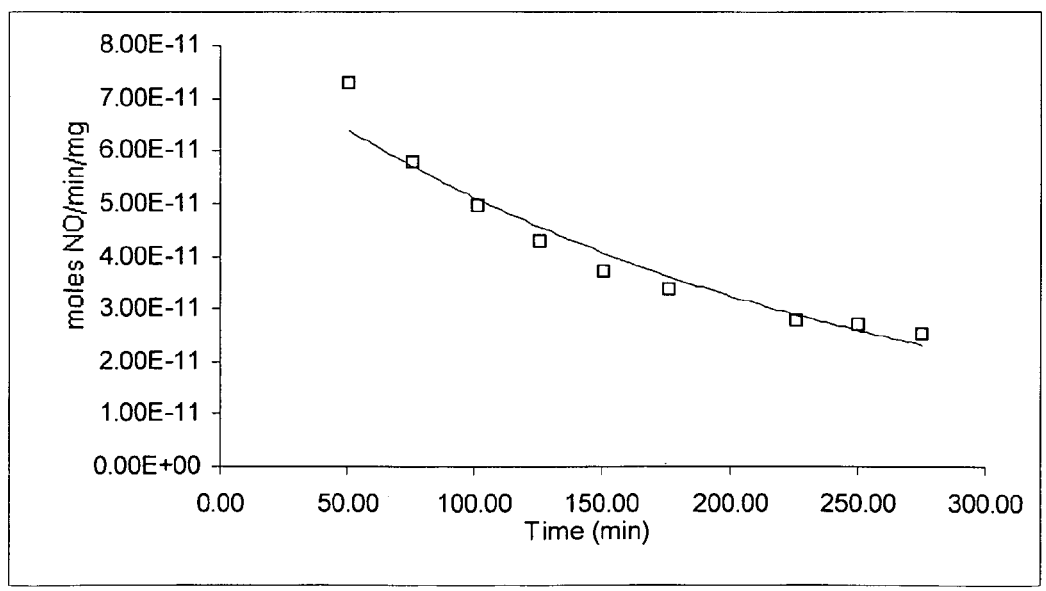

The diazeniumdiolated polyacrylonitrile powder of Example 2 was slurried in pH 7.4 phosphate buffer at 37° C. The release of NO was monitored by detection of the chemiluminescence generated by treatment of the effluent gas steam with ozone. FIG. 1 shows the (a) short term and (b) long term release profiles. This material released a total of $6.57 \times 10^{-8}$ moles NO/mg before the release fell below the detection threshold after three days.

Example 9

This example describes the release of NO from diazeniumdiolated poly(styrene-co-acrylonitrile) powder.

Figure 2A:
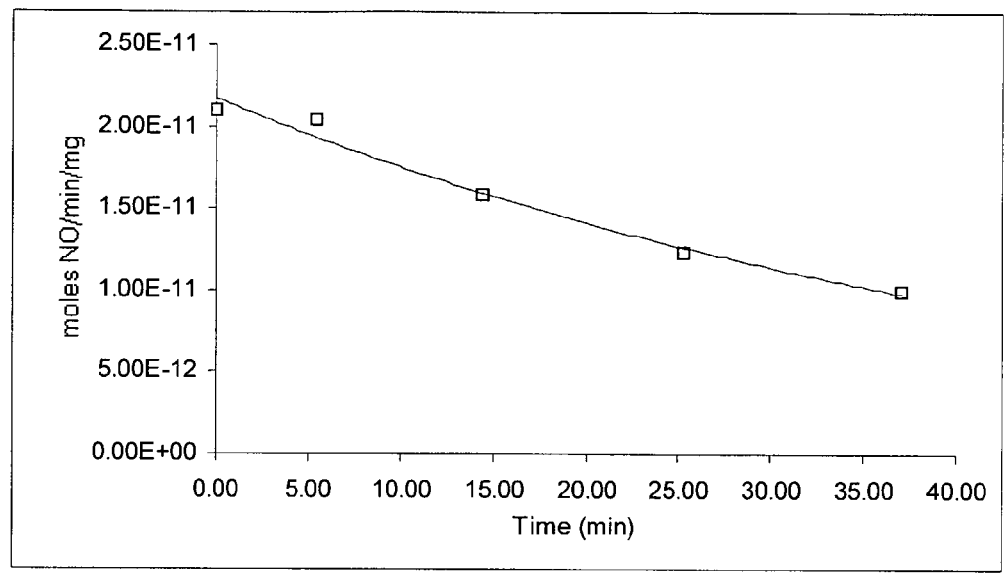
FIG. 2 is a time course of NO release from diazeniumdiolated poly(styrene-co-acrylonitrile) powder over (a) 40 minutes and (b) 5,000 minutes.
Figure 2B:
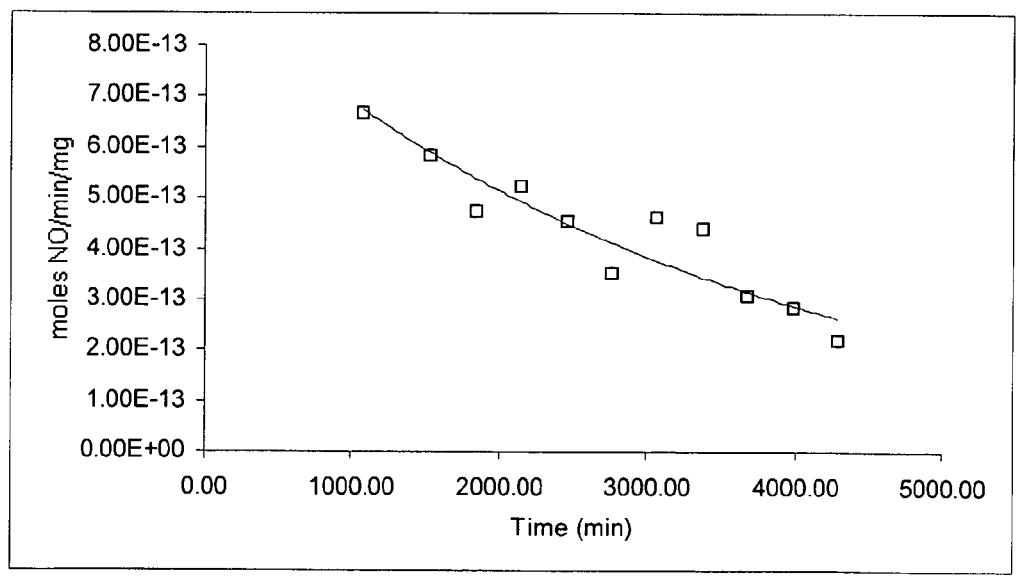

The diazeniumdiolated poly(styrene-co-acrylonitrile) powder of Example 3 was slurried in pH 7.4 phosphate buffer at 37° C., and the release of NO monitored by detection of the chemiluminescence generated by treatment of the effluent gas steam with ozone. FIG. 2 shows the (a) short term and (b) long term release profiles. This material released a total of $3.68 \times 10^{-9}$ moles NO/mg before the release fell below the detection threshold after three days.

Example 10

This example describes the release of NO from diazeniumdiolated nitrile rubber glove pieces.

Figure 3A:
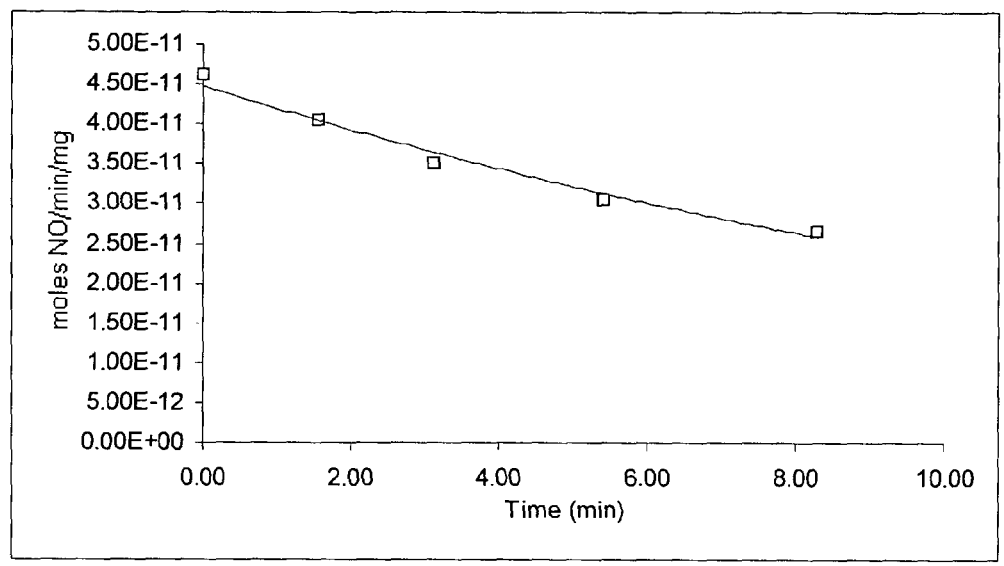
FIG. 3 is a time course of NO release from diazeniumdiolated nitrile rubber glove pieces over (a) 10 minutes and (b) 3,000 minutes.
Figure 3B:
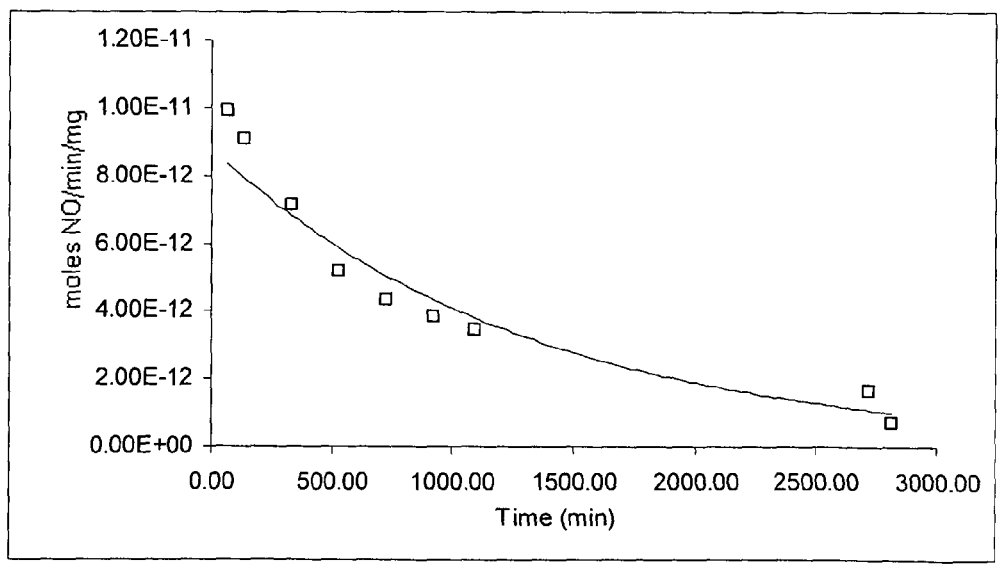

The diazeniumdiolated nitrile rubber glove pieces of Example 5 were slurried in pH 7.4 phosphate buffer at 37° C., and the release of NO monitored by detection of the chemiluminescence generated by treatment of the effluent gas steam with ozone. FIG. 3 shows the (a) short term and (b) long term release profiles. This material released a total of $2.13 \times 10^{-8}$ moles NO/mg before the release fell below the detection threshold after seven days.

Example 11

This example describes the release of NO from diazeniumdiolated acrylic yarn.

Figure 4A:
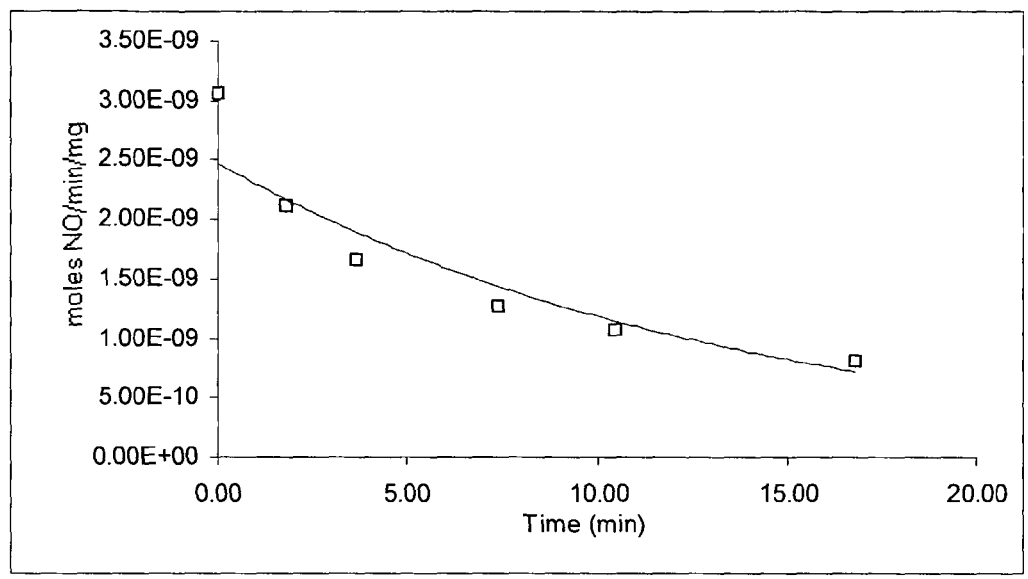
FIG. 4 is a time course of NO release from diazeniumdiolated acrylic yarn over (a) 20 minutes and (b) 300 minutes.
Figure 4B:
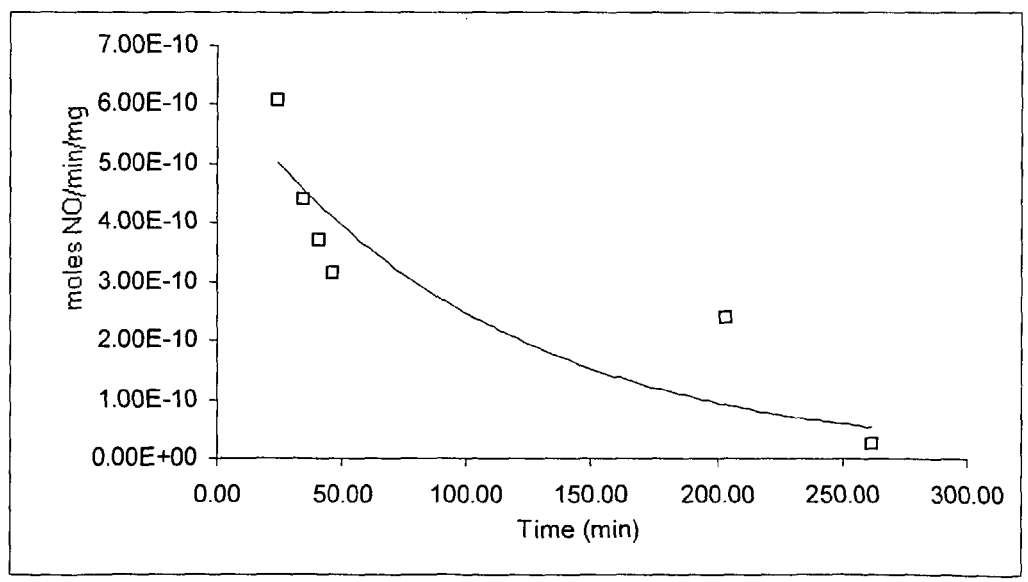

The diazeniumdiolated acrylic yarn of Example 6 was slurried in pH 7.4 phosphate buffer at 37° C., and the release of NO monitored by detection of the chemiluminescence generated by treatment of the effluent gas steam with ozone. FIG. 4 shows two short term release profiles. This material released a total of $2.23 \times 10^{-9}$ moles NO/mg in the first four hours, and NO release was still detectable after three days.

Example 12

This example describes the release of NO from diazeniumdiolated polyacrylonitrile hollow filter fibers.

Figure 5A:
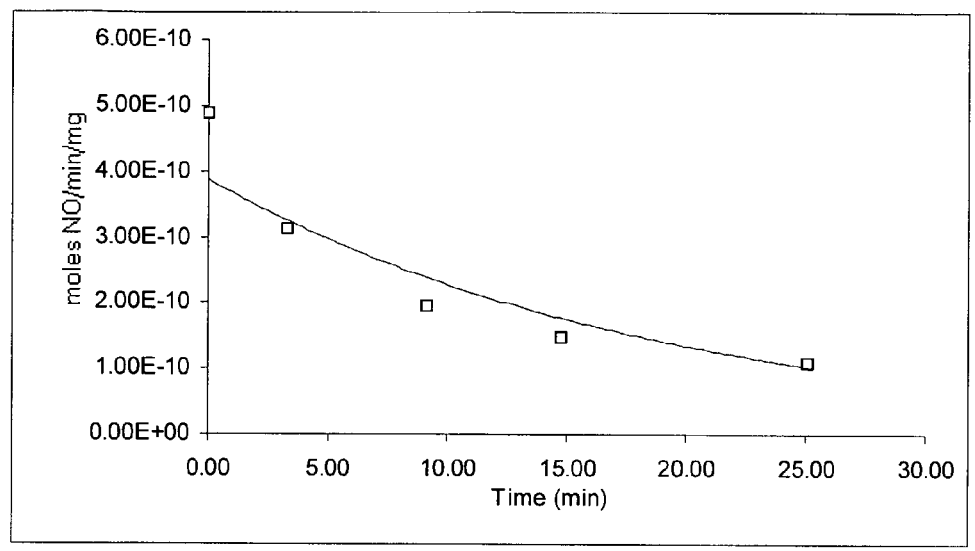
FIG. 5 is a time course of NO release from diazeniumdiolated polyacrylonitrile hollow filter fibers over (a) 30 minutes and (b) 300 minutes.
Figure 5B:
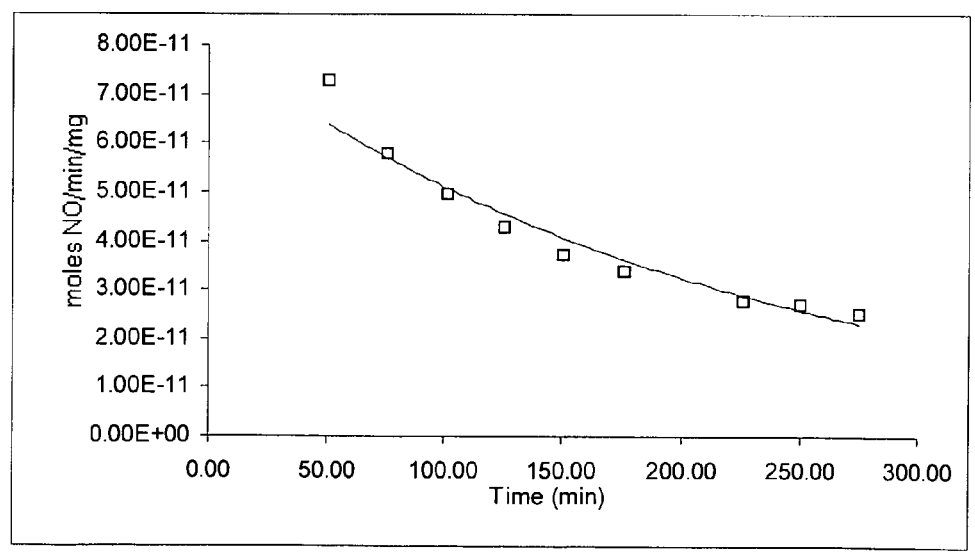

The diazeniumdiolated polyacrylonitrile hollow filter fibers of Example 8 were slurried in pH 7.4 phosphate buffer at 37° C., and the release of NO monitored by detection of the chemiluminescence generated by treatment of the effluent gas steam with ozone. FIG. 5 shows two short term release profiles. This material released a total of $9.8 \times 10^{-9}$ moles NO/mg over the first five hours, and was still well above the limit of detection at that point.

Example 13

Several small molecule analogs were synthesized to serve as models of diazeniumdiolated polyacrylonitrile. This example describes the preparation of compounds of formula (I) and (II).

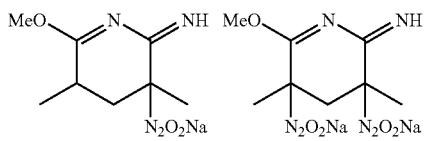

The synthesis of 2,4-dicyanopentane was previously reported by Takata et al. and later by Clark (Takata et al., Chem. High Polym. Jap., 16: 693 (1959) and Clark, H. G., Makrom. Chem., 63: 69 (1963)). A solution of 2,4-dicyanopentane (0.10 g, 8.2×10-4 mol) in 25% NaOMe/MeOH (0.35 g, 1.6×10-3 mol) was prepared in a vial which was placed into a 250 mL glass Parr hydrogenation bottle and purged with argon. The solution was then placed under approximately 80 psi of NO gas and stirred at ambient temperature for 24 hours. During this time, a small amount of white precipitate formed. Upon completion, the pressure was released, and the solution was purged with argon. The white precipitate was filtered, washed with diethyl ether, and dried in vacuo, resulting in a white powder. Yield: 11.6 mg (6.0%).

Example 14

This example describes an alternative preparation of compounds of formula (I) and (II).

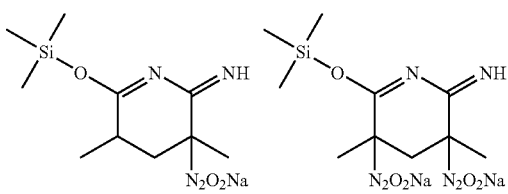

A solution of 2,4-dicyanopentane (0.50 g, $4.1 \times 10^{-3}$ mol, prepared by slight modification of the previously reported procedures and having a meso:racemate ratio of 1:1) in anhydrous dioxane (7 mL) was prepared in a vial and treated with sodium trimethylsilanoate (0.92 g, $8.2 \times 10^{-3}$ mol). The vial was placed into a 250 mL glass Parr hydrogenation bottle and purged with argon. The solution was then placed under approximately 80 psi of NO gas and stirred at ambient temperature for 48 hours. During this time a white precipitate formed. After 48 h, the pressure was released, and the solution was purged with argon. The white precipitate was filtered, rinsed with dioxane followed by diethyl ether and dried in vacuo resulting in a white powder. Yield: 375 mg (31.0%).

Example 15

This example describes another alternative preparation of compounds of formulas (I) and (II).

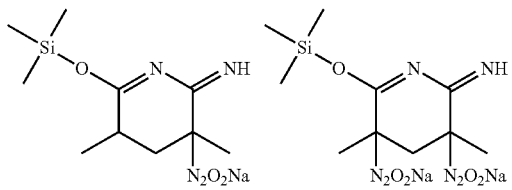

A solution of 2,4-dicyanopentane (1.00 g, 8.20 mmol) in anhydrous THF (2 mL) was prepared in a vial and treated with a solution of sodium trimethylsilanoate (2.3 g, 20.5 mmol) in anhydrous THF (4 mL). The vial was placed into a 250 mL glass Parr hydrogenation bottle and purged with argon. The solution was then placed under approximately 80 psi of NO gas and stirred at ambient temperature for 72 hours. During this time, a large amount of white precipitate formed. Upon completion, the pressure was released and the solution was purged with argon. The white precipitate was filtered, rinsed with THF, then ether and dried in vacuo resulting in 1.19 g (crude yield, 38.6%) of a white powder.

Example 16

This example describes the preparation of compounds of formula (VI) and (VII).

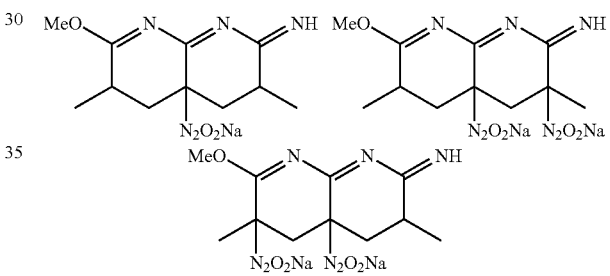

2,4,6-Tricyanoheptane was prepared as reported by Takata et al., Chem. High Polym. Jap., 16: 693 (1959). A solution of 2,4,6-tricyanoheptane (0.10 g, $5.7 \times 10^{-4}$ mol) in anhydrous dioxane (3 mL) was prepared in a vial and treated with sodium trimethylsilanoate (0.07 g, $1.2 \times 10^{-3}$ mol). The vial was placed into a 250 mL glass Parr hydrogenation bottle and purged with argon. The solution was then placed under approximately 80 psi of NO gas and stirred at ambient temperature for 48 hours. During this time a light yellow precipitate formed. After 48 h, the pressure was released, and the solution was purged with argon. The yellow precipitate was filtered, rinsed with dioxane followed by diethyl ether and dried in vacuo resulting in a light yellow powder. Yield: 110 mg (55.6%).

Example 17

This example describes the NO release profile of the compounds of Example 13.

Figure 6:
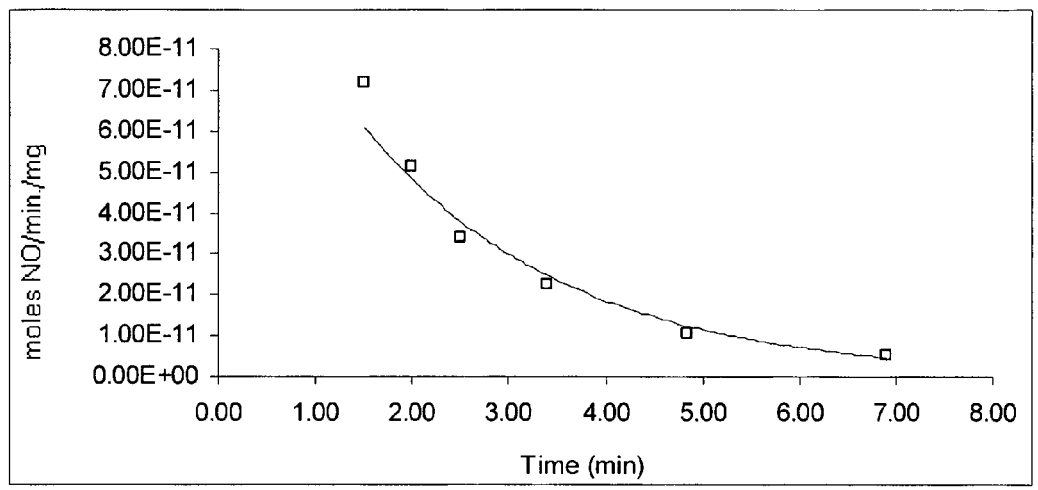
FIG. 6 is a time course of NO release from diazeniumdiolated 2,4-dicyanopentane as prepared in Example 14.

The diazeniumdiolated 2,4-dicyanopentane product prepared in Example 13 was dissolved in pH 7.4 phosphate buffer at 37° C., and the release of NO was monitored by detection of the chemiluminescence generated by treatment of the effluent gas steam with ozone. FIG. 6 shows the release profile of this compound.

Example 18

This example describes the NO release profile of the compounds of Example 16.

Figure 7:
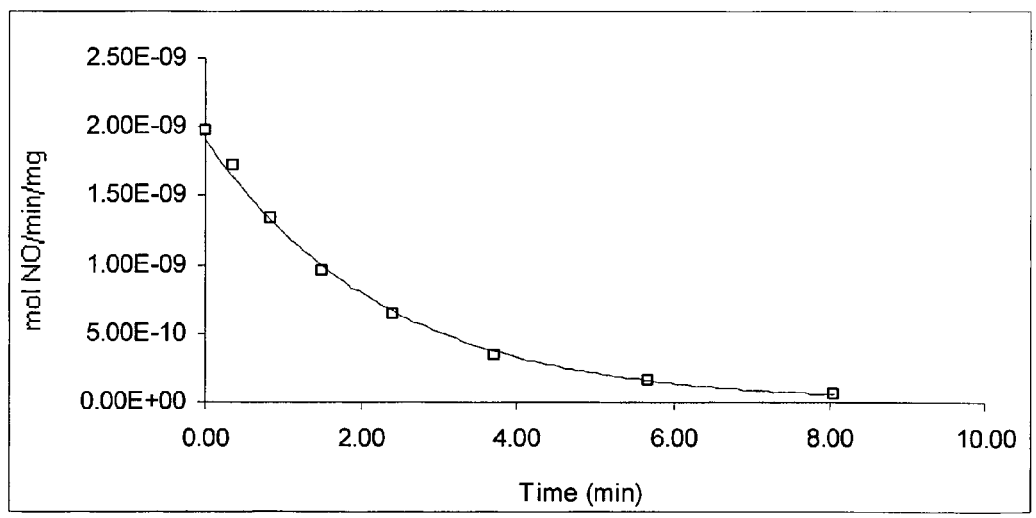
FIG. 7 is a time course of NO release from diazeniumdiolated 2,4,6-tricyanopentane as prepared in Example 16.

The diazeniumdiolated 2,4,6-tricyanopentane product was dissolved in pH 7.4 phosphate buffer at 37° C. and the release of NO was monitored by detection of the chemiluminescence generated by treatment of the effluent gas steam with ozone. FIG. 7 shows the release profile of this compound.

Example 19

This example describes the preparation of a compound of formula (IV).

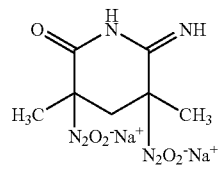

Crude material prepared in Examples 13, 14, and 15 was treated as follows: crude material was dissolved in a minimum amount of water and precipitated by addition of a ten-fold excess of methanol followed by cooling with dry ice for approximately one hour. The resulting suspension was centrifuged and the supernatant was decanted. The resulting solid was re-suspended in methanol, filtered, rinsed with methanol, then ether, and dried in vacuo, resulting in a white powder. The powder was re-dissolved in a minimum amount of water and chromatographed on silica using a 4:1 acetonitrile:water eluent followed by a 1:1 acetonitrile:water mixture resulting in two fractions. The second fraction was the desired compound. Purified compound was thus characterized: UV/Vis (0.01 M aq. NaOH) $\{\lambda_{max}$ in nm ($\epsilon$ in mM$^{-1}$ cm$^{-1}$)$\}$ 250 (21.0). ESI-MS (−): 259 m/z (M$^{2-}$+H$^{+}$) (calc.). found 259. Hi-Res ESI-MS (−): 259.079 (calc.). found 259.075. $^{1}$H NMR (D$_{2}$O): δ 1.68 (s, 3H), 1.85 (s, 3H), 2.35 (d, 1H), 3.44 (d, 1H). $^{13}$C NMR (D$_{2}$O): δ 26.6, 28.1, 42.4, 70.3, 72.8, 175.1, 181.3.

Example 20

This example describes the preparation of a compound of formula (V).

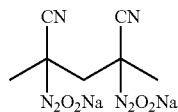

Crude material prepared in Examples 13, 14, and 15 was treated as follows: crude material was dissolved in a minimum amount of water and precipitated by addition of a ten-fold excess of methanol followed by cooling with dry ice for approximately one hour. The resulting suspension was centrifuged and the supernatant was decanted. The resulting solid was re-suspended in methanol, filtered, rinsed with methanol, then ether, and dried in vacuo, resulting in a white powder. The powder was re-dissolved in a minimum amount of water and chromatographed on silica using a 4:1 acetonitrile:water eluent followed by a 1:1 acetonitrile:water mixture resulting in two fractions. The first fraction was the desired compound. Purified compound was thus characterized: UV/Vis (0.01 M aq. NaOH) $\{\lambda_{max}$ in nm ($\epsilon$ in mM$^{-1}$ cm$^{-1}$)$\}$ 253 (17.0). ESI-MS (−): 241 m/z (M$^{2-}$+H$^{+}$) (calc.). found 241. Hi-Res ESI-MS (−): 241.068 (calc.). found 241.067. $^{1}$H NMR (D$_{2}$O): δ 2.00 (s, 6H), 3.06 (d, 1H), 3.28 (d, 1H). $^{13}$C NMR (D$_{2}$O): δ 27.2, 44.2, 66.7, 120.1.

Example 21

This example describes the NO-release profile of the compound of Example 19.

Figure 8A:
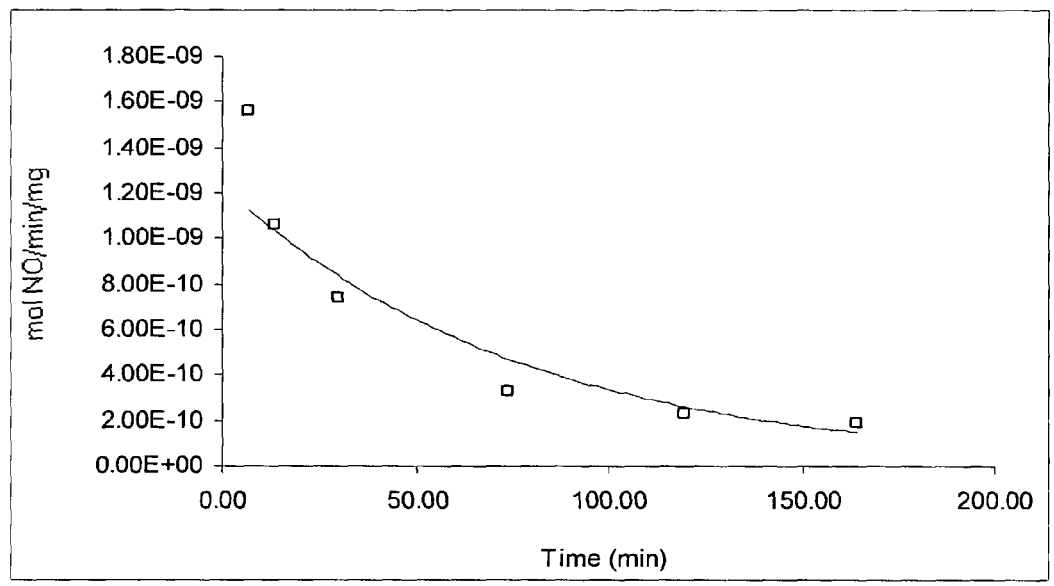
FIG. 8 is a time course of NO release from diazeniumdiolated 2,4-dicyanopentane as prepared in Example 19 prior to chromatography (approximately 95:5 IV:V) over (a) 160 minutes and (b) 194 days.
Figure 8B:
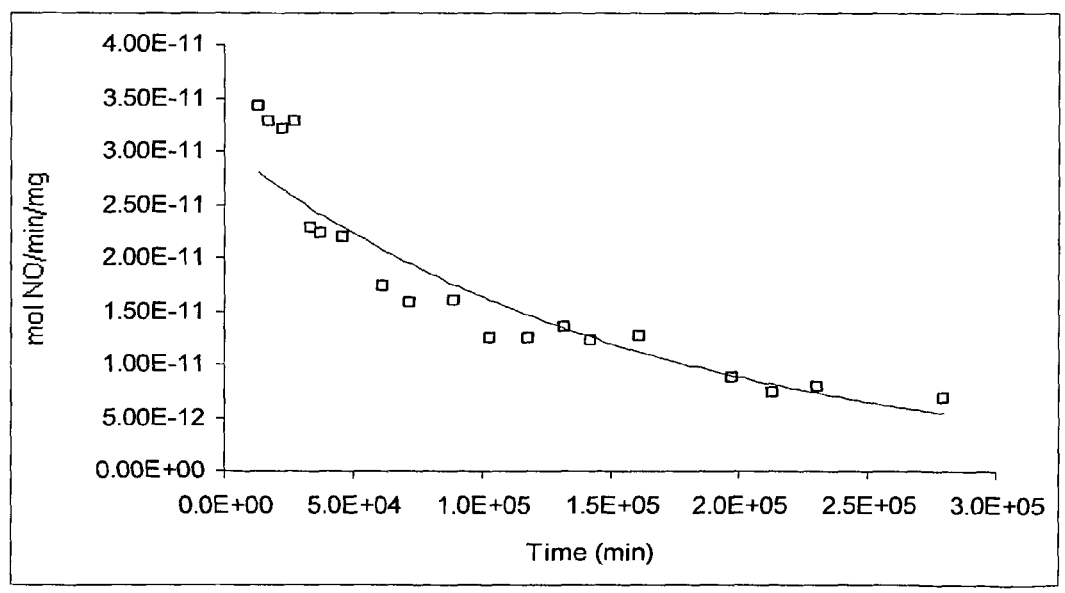

The diazeniumdiolated 2,4-dicyanopentane product was dissolved in pH 7.4 phosphate buffer at 37° C. and the release of NO was monitored by detection of the chemiluminescence generated by treatment of the effluent gas steam with ozone. FIG. 8 shows the (a) short term and (b) long term release profiles.

Example 22

This example describes the preparation of a compound of formula (X).

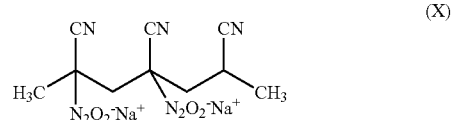

The crude material from Example 16 was dissolved in a minimum amount of water and precipitated by addition of a ten-fold excess of acetone followed by cooling with dry ice for approximately one hour. The resulting suspension was centrifuged and the supernatant was decanted. The resulting solid was re-suspended in acetone, filtered, rinsed with acetone, then ether, and dried in vacuo, resulting in a white powder. Yield: 0.400 g (16%). UV/Vis (0.01 M aq. NaOH) $\{\lambda_{max}$ in nm ($\epsilon$ in mM$^{-1}$ cm$^{-1}$)$\}$ 250 (22.3), 300 sh (2.4). ESI-MS (−): 294 m/z (M$^{2-}$+H$^{+}$) (calc.). found 294. $^{1}$H NMR (D$_{2}$O): 1.44 (d, 3H); 2.02 (s, 3H); 2.36 (dd, 1H); 2.87 (dd, 1H); 3.04 (d, 1H); 3.09-3.16 (m, 1H); 3.31 (d, 1H). $^{13}$C NMR: 20.7, 24.0, 26.0, 42.7, 43.9, 67.1, 68.6, 117.8, 120.3, 124.8.

Example 23

This example describes the NO-release profile of the compound of Example 22.

Figure 9A:
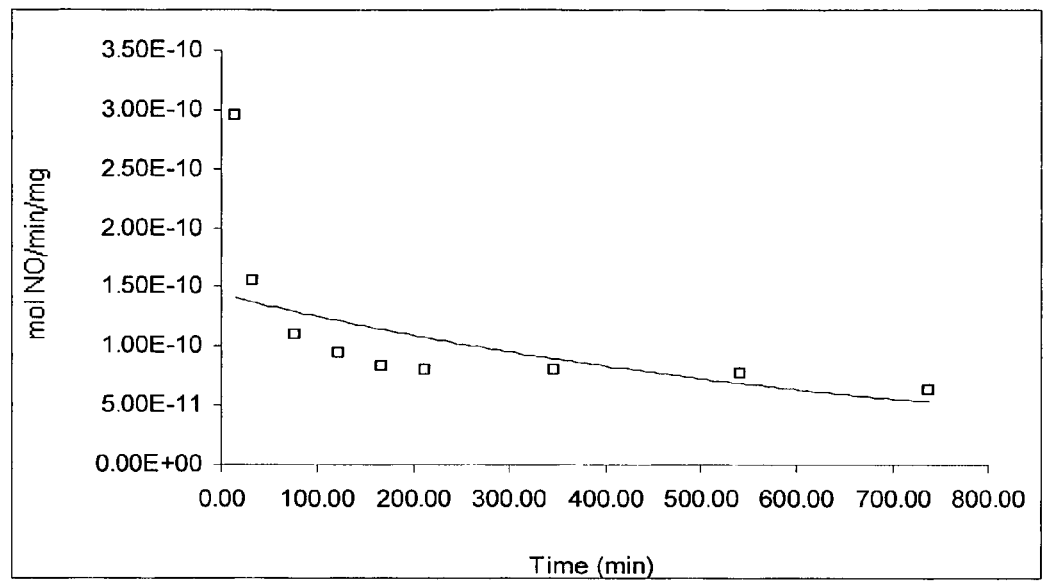
FIG. 9 is time course of NO release from diazeniumdiolated 2,4,6-tricyanopentane as prepared in Example 22 over (a) 730 minutes and (b) 194 days.
Figure 9B:
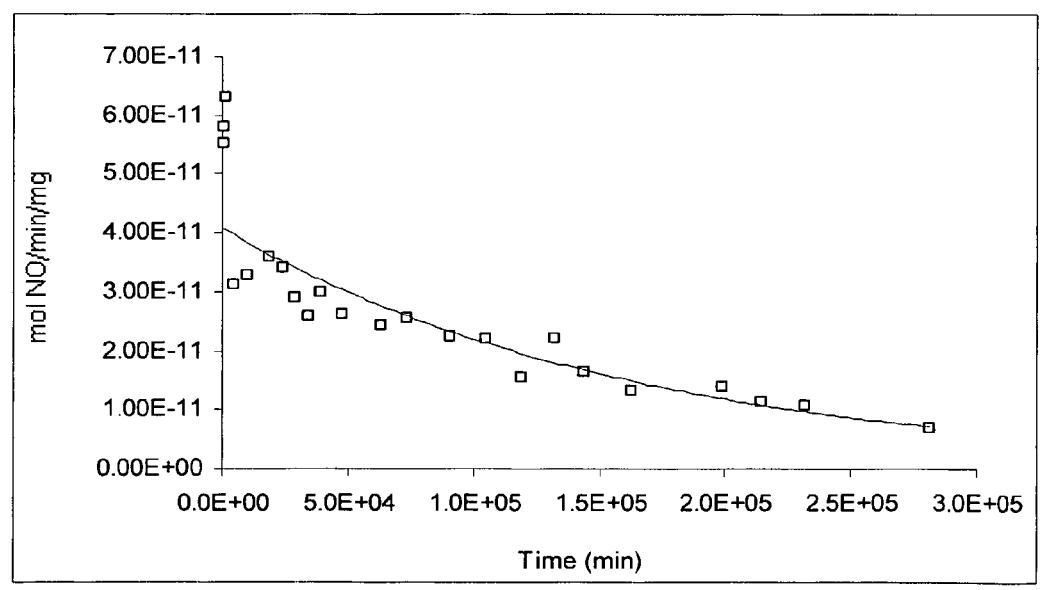

The diazeniumdiolated 2,4,6-tricyanopentane product was dissolved in pH 7.4 phosphate buffer at 37° C. and the release of NO was monitored by detection of the chemiluminescence generated by treatment of the effluent gas steam with ozone. FIG. 9 shows the (a) short term and (b) long term release profiles.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A nitric oxide-releasing acrylonitrile-based polymer comprising at least two adjacent units derived from acrylonitrile monomer and at least one nitric oxide releasing $N_2O_2^-$ group, wherein the $N_2O_2^-$ group is attached directly to a carbon atom in the polyacrylonitrile backbone.

2. The polymer of claim 1, wherein the polymer is polyacrylonitrile (PAN).

3. The polymer of claim 1, wherein the polymer is a copolymer comprising at least two adjacent units derived from acrylonitrile monomer.

4. The polymer of claim 3, wherein the copolymer further comprises at least one comonomer selected from the group consisting of styrene, divinylbenzene, 4-methylstyrene, 4-chloromethylstyrene, 4-aminostyrene, 4-chlorostyrene, 4-bromostyrene, 4-vinylphenol, 4-vinylpyridine, 2-vinylpyridine, butadiene, 2-chlorobutadiene, acrylic acid, methacrylic acid, methyl methacrylate, ethyl methacrylate, acrylamide, methylacrylonitrile, ethylene, propylene, isoprene, acrolein, methacrolein, 1-glycerol methacrylate, 2-hydroxyethyl methacrylate, 2-hydroxypropyl methacrylate, vinyl alcohol, allyl alcohol, allyl acetate, vinyl acetate, allylamine, vinylamine, N-methyl vinylamine, N-methyl allylamine, N,N-dimethyl vinylamine, N,N-dimethyl allylamine, isopropenyl acetate, tetrafluoroethylene, chlorotrifluoroethylene, dichloroethylene, vinylidene difluoride, vinylchloride, N-vinylpyrrolidone, ethylenimine, ethyleneglycol, ethylene oxide, tetrahydrofuran, glycidyl acrylate, glycidyl methacrylate, lactate, glycolate, urethane, combinations, and mixtures thereof.

5. The polymer of claim 4, wherein the comonomer is butadiene.

6. The polymer of claim 4, wherein the comonomer is styrene.

7. The polymer of claim 1, wherein at least one $N_2O_2^-$ group is bonded to the carbon that originally contained the cyano substituent.

8. The polymer of claim 1, wherein the polymer is bound to a substrate.

9. The polymer of claim 8, wherein the substrate comprises metal, glass, ceramic, or plastic or rubber.

10. A pharmaceutical composition comprising at least one polymer of claim 1 and a carrier.

11. A medical device comprising a polymer of claim 1.

12. The medical device of claim 11, wherein the device is selected from the group consisting of a blood oxygenator, blood pump, blood storage bag, blood collection tube, blood filter, dialysis membrane, tubing, a vascular graft, stent, pacemaker lead, surgical prosthetic conduit, heart valve, a catheter, guide wire, amniocentesis needle, biopsy needle, cannula, drainage tube, shunt, sensor, transducer, probe, an artificial joint, an artificial heart, a penile implant, condom, tampon, sanitary napkin, ocular lens, sling material, suture, hemostat, antimicrobial material, surgical mesh, transdermal patch, and wound dressings/bandages.

13. A method for treating a biological disorder in a mammal in which dosage with nitric oxide is beneficial, comprising administering to the mammal the medical device of claim 11 to a specific location on or within the mammal in an amount sufficient to release a therapeutically effective amount of nitric oxide.

14. The method of claim 13, wherein the biological disorder is selected from the group consisting of hypertension, restenosis, cancer, impotency, platelet aggregation, viral or parasitic infection, bacterial infection, and fungal infection.

15. A method for promoting angiogenesis in a tissue of a mammal in need thereof, comprising administering to the mammal, the medical device of claim 11 to a specific location on or within the mammal in an amount effective to promote angiogenesis in the tissue.

16. The method of claim 15, wherein the mammal has a condition selected from the group consisting of hypertension, diabetic peripheral vascular disease, gangrene, Buerger's syndrome, a wound, ischemia of the muscle, brain, kidney, lung, heart or limb, severe occlusive and/or obstructive vascular disease, peripheral vascular disease, myocardial ischemia, myocardial infarction, coronary artery disease, cerebral vascular disease, and visceral vascular disease.

* * * * *